(12) United States Patent
Nakayama et al.

(10) Patent No.: US 12,357,254 B2
(45) Date of Patent: Jul. 15, 2025

(54) RADIOGRAPHY SYSTEM, OPERATION METHOD OF RADIOGRAPHY SYSTEM, AND RADIOGRAPHY CONTROL APPARATUS

(71) Applicant: FUJIFILM Corporation, Tokyo (JP)

(72) Inventors: Hiroki Nakayama, Kanagawa (JP); Riki Igarashi, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 221 days.

(21) Appl. No.: 18/448,448

(22) Filed: Aug. 11, 2023

(65) Prior Publication Data

US 2024/0050055 A1 Feb. 15, 2024

(30) Foreign Application Priority Data

Aug. 12, 2022 (JP) ................. 2022-129033

(51) Int. Cl.
*A61B 6/50* (2024.01)
*A61B 6/00* (2006.01)
*A61B 6/46* (2024.01)

(52) U.S. Cl.
CPC ............ *A61B 6/502* (2013.01); *A61B 6/461* (2013.01); *A61B 6/545* (2013.01); *A61B 6/547* (2013.01)

(58) Field of Classification Search
CPC ......... A61B 6/502; A61B 6/461; A61B 6/545; A61B 6/547; A61B 6/04; A61B 6/0414
See application file for complete search history.

(56) References Cited

U.S. PATENT DOCUMENTS

2015/0109304 A1* 4/2015 Isokawa ................. A61B 6/461 345/427
2021/0307711 A1 10/2021 Vancamberg et al.

FOREIGN PATENT DOCUMENTS

JP 2021-164641 A 10/2021

\* cited by examiner

*Primary Examiner* — Kiho Kim
(74) *Attorney, Agent, or Firm* — Studebaker Brackett PLLC

(57) ABSTRACT

A radiography system includes a radiography apparatus, a distance measurement device, and a processor. The processor generates subject posture information indicating a posture of a subject based on distance measurement information generated by the distance measurement device, generates positional relationship estimation information indicating a position, a posture, and/or an orientation of the subject with respect to the radiography apparatus by using the subject posture information and apparatus posture information indicating a posture of the radiography apparatus, and performs notification control of giving notification about capturing of the radiation image and/or imaging apparatus control with respect to the radiography apparatus based on the positional relationship estimation information.

15 Claims, 11 Drawing Sheets

FIG. 13
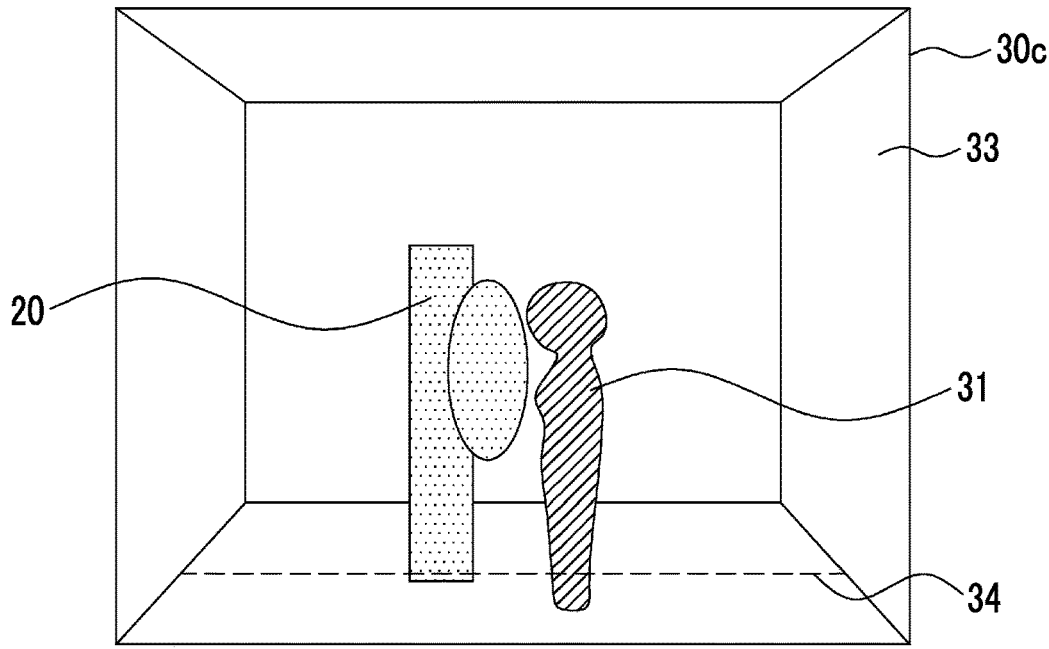
FIG. 14
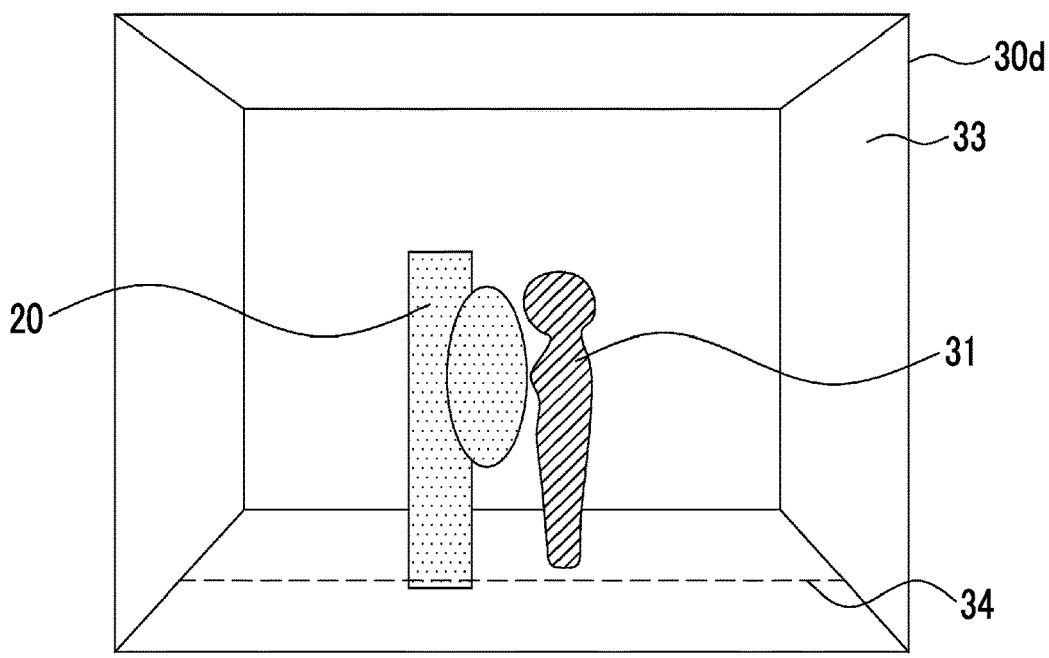
FIG. 15
| IMAGING SUPPORT INFORMATION GENERATION UNIT | 71 |
| IMAGING POSITION INFORMATION GENERATION UNIT | 120 |

RADIOGRAPHY SYSTEM, OPERATION METHOD OF RADIOGRAPHY SYSTEM, AND RADIOGRAPHY CONTROL APPARATUS

CROSS-REFERENCE TO RELATED APPLICATIONS

This application claims priority under 35 U.S.C § 119(a) to Japanese Patent Application No. 2022-129033 filed on 12 Aug. 2022. The above application is hereby expressly incorporated by reference, in its entirety, into the present application.

BACKGROUND OF THE INVENTION

1. Field of the Invention

The present invention relates to a radiography system that supports imaging of a radiation image by using posture information of a subject, an operation method of the radiography system, and a radiography control apparatus.

2. Description of the Related Art

In mammography, a technique of adjusting a position of a detector by using a camera image in order to capture an appropriate radiation image is known. For example, in JP2021-164641A (corresponding to US2021/307711A1), it is described that "A controller can evaluate a height of the user based on a camera image of a user from a vision system, and can automatically adjust a position of a compression paddle and/or a detector based on the height of the user for clean QC and/or cleaning".

SUMMARY OF THE INVENTION

In JP2021-164641A, the position of the detector is adjusted by using a camera image in which the subject is imaged. However, since a main subject of the mammography is a woman, obtaining the camera image of the subject before an examination or during the examination may impose a psychological burden on the subject. In a case in which a resolution of the camera image is lowered to a level at which the psychological burden is not imposed, there is a risk that the subject cannot be appropriately extracted from the image and the accuracy of the extraction result cannot be guaranteed.

The present invention is to provide a radiography system capable of supporting capturing of a radiation image while reducing a psychological burden on a subject, an operation method of the radiography system, and a radiography control apparatus.

A radiography system according to an aspect of the present invention comprises a radiography apparatus, a distance measurement device, and a processor. The radiography apparatus generates a radiation image by imaging a subject. The distance measurement device generates distance measurement information about a detection target including the subject. The processor acquires the distance measurement information, generates subject posture information indicating a posture of the subject based on the distance measurement information, generates positional relationship estimation information indicating a position, a posture, and/or an orientation of the subject with respect to the radiography apparatus by using the subject posture information and apparatus posture information indicating a posture of the radiography apparatus, and performs notification control of giving notification about capturing of the radiation image and/or imaging apparatus control with respect to the radiography apparatus based on the positional relationship estimation information.

It is preferable that the distance measurement device generates distance measurement information about the radiography apparatus, and the processor generates the apparatus posture information based on the distance measurement information.

It is preferable that the processor acquires the apparatus posture information by using a positional relationship, which is input in advance, between the distance measurement device and the radiography apparatus.

It is preferable that the subject posture information includes body axis information indicating a position of a body axis in a cranio-caudal direction of the subject, and the processor generates imaging position information, which is a result of a determination as to whether the body axis in the cranio-caudal direction of the subject is a right breast imaging position that is a position for imaging a right breast of the subject or a left breast imaging position that is a position for imaging a left breast of the subject, as the positional relationship estimation information by using the body axis information and the apparatus posture information.

It is preferable that the processor performs the notification control of giving notification that the radiography apparatus captures the radiation image of the left breast of the subject or the right breast of the subject based on the imaging position information.

It is preferable that the processor generates imaging preparation comparison information, which is a result of a comparison between the imaging position information and imaging preparation information, which is input in advance, for giving an instruction to image the left breast or the right breast of the subject, and performs the notification control or the imaging apparatus control based on the imaging preparation comparison information.

It is preferable that the radiography apparatus includes an imaging table on which a breast of the subject is disposed, and a movable portion that moves in a vertical direction or rotates while maintaining a position relative to a radiation source that generates radiation, and the apparatus posture information includes movable portion position information indicating a position of the movable portion.

It is preferable that the subject posture information includes breast position information indicating a position of a left breast and/or a right breast of the subject, and the processor generates the positional relationship estimation information indicating a position of the left breast or the right breast of the subject with respect to the movable portion based on the breast position information and the movable portion position information, and performs the notification control of giving notification that a distance between the position of the breast and the position of the movable portion is equal to or greater than a specific imaging distance based on the positional relationship estimation information.

It is preferable that the subject posture information includes breast position information indicating a position of a left breast and/or a right breast of the subject, and the processor generates the positional relationship estimation information indicating a position of the left breast or the right breast of the subject with respect to the movable portion based on the breast position information and the movable portion position information, and performs the imaging apparatus control of moving or rotating the movable portion based on the positional relationship estimation information.

It is preferable that the distance measurement device generates the distance measurement information about an examiner different from the subject, and the processor generates examiner posture information indicating a posture of the examiner based on the distance measurement information, generates examiner positional relationship estimation information indicating a position, a posture, and/or an orientation of the examiner with respect to the movable portion based on the examiner posture information and the movable portion position information, and performs the notification control of giving notification to the examiner and/or the imaging apparatus control of stopping the movable portion based on the examiner positional relationship estimation information.

It is preferable that the processor generates imaging support information for giving an instruction to perform the imaging apparatus control of releasing a sleep mode of the radiography apparatus based on the positional relationship estimation information.

It is preferable that the distance measurement device emits a detection signal toward a back surface or a side surface of the subject.

It is preferable that the processor inputs the distance measurement information to a trained model and outputs the subject posture information.

An operation method of a radiography system according to an aspect of the present invention comprises a step of generating distance measurement information about a detection target including a subject, a step of acquiring the distance measurement information, a step of generating subject posture information indicating a posture of the subject based on the distance measurement information, a step of generating positional relationship estimation information indicating a position, a posture, and/or an orientation of the subject with respect to a radiography apparatus that generates a radiation image by imaging the subject, by using the subject posture information and apparatus posture information indicating a posture of the radiography apparatus, and a step of performing notification control of giving notification about capturing of the radiation image and/or imaging apparatus control with respect to the radiography apparatus based on the positional relationship estimation information.

A radiography control apparatus according to an aspect of the present invention performs notification control of giving notification about capturing of a radiation image and/or imaging apparatus control with respect to a radiography apparatus based on positional relationship estimation information indicating a position, a posture, and/or an orientation of a subject with respect to the radiography apparatus, which is obtained from subject posture information obtained from distance measurement information from a distance measurement device and apparatus posture information indicating a positional relationship of the radiography apparatus.

According to the present invention, it is possible to support the capturing of the radiation image while reducing the psychological burden on the subject.

BRIEF DESCRIPTION OF THE DRAWINGS

FIG. 13 is an explanatory diagram showing an example of distance measurement information generated in a case in which the distance measurement device is disposed on the side surface of the subject at the position at which the detection signal is emitted and the position of the subject is the right breast imaging position.

FIG. 14 is an explanatory diagram showing an example of distance measurement information generated in a case in which the distance measurement device is disposed on the side surface of the subject at the position at which the detection signal is emitted and the position of the subject is the left breast imaging position.

FIG. 15 is a block diagram showing a function of an imaging position information generation unit.

DESCRIPTION OF THE PREFERRED EMBODIMENTS

First Embodiment

Figure 1:
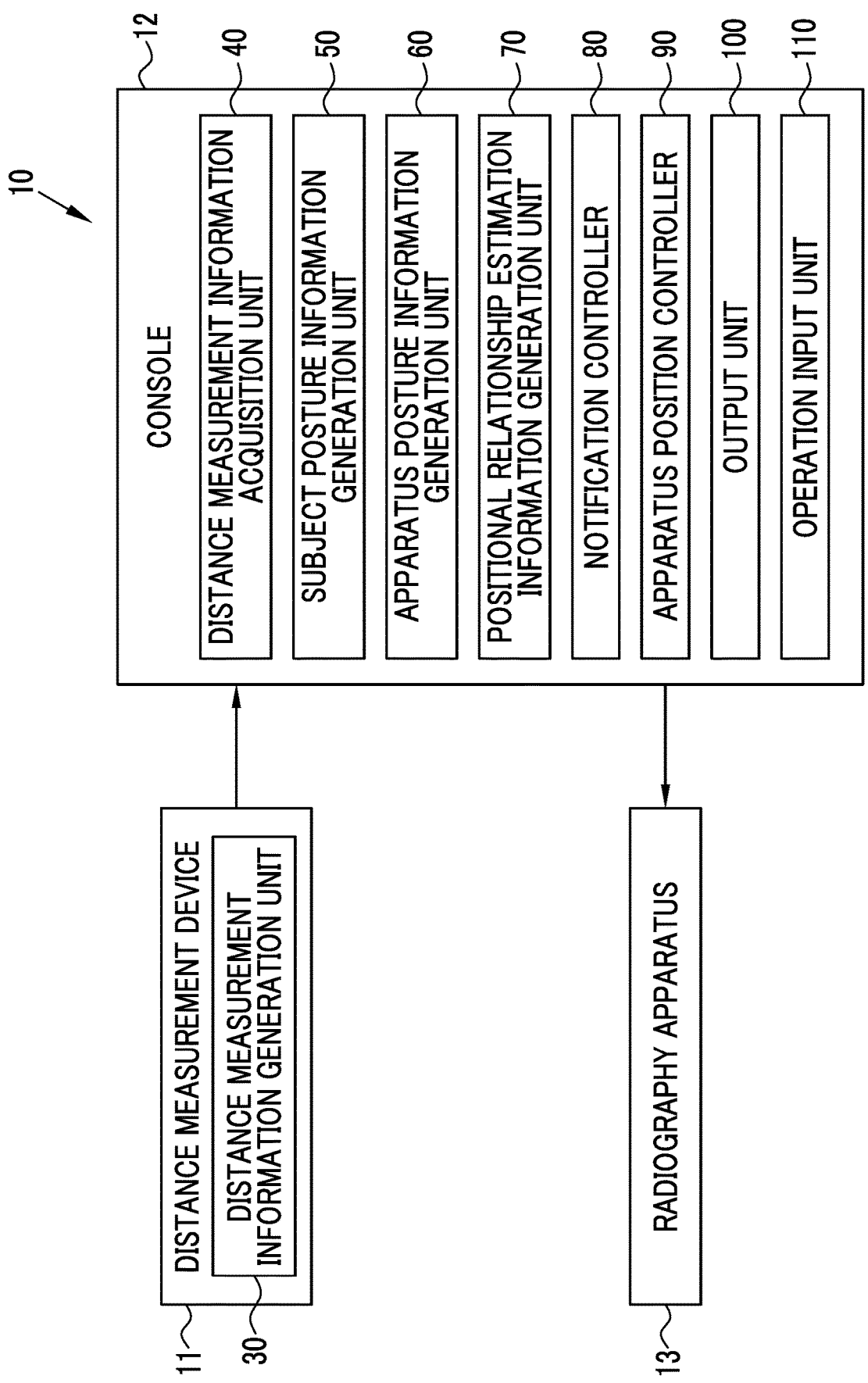
FIG. 1 is a block diagram showing a function of a radiography system.

As shown in FIG. 1, a radiography system 10 comprises a distance measurement device 11, a console 12, and a radiography apparatus 13. The distance measurement device 11 acquires distance measurement information by using a reflection signal obtained by transmitting a detection signal. The console 12 comprehensively controls the radiography system 10. Also, the console 12 controls the radiography apparatus 13. In addition, the console 12 acquires the distance measurement information from the distance measurement device 11 and uses the distance measurement information to perform imaging support control on an output unit 100 of the console 12 and/or the radiography apparatus 13. The imaging support control includes notification control and imaging apparatus control. The radiography system 10 supports capturing of a radiation image by performing the notification control and/or the imaging apparatus control.

The distance measurement device 11, the console 12, and the radiography apparatus 13 are connected to each other in a communicable manner by a wired or wireless network. The wireless network is, for example, the Internet or a local area network (LAN).

As shown in FIG. 1, the distance measurement device 11 includes a distance measurement information generation unit 30. The console 12 includes a distance measurement information acquisition unit 40, a subject posture information generation unit 50, an apparatus posture information generation unit 60, a positional relationship estimation information generation unit 70, a notification controller 80, an apparatus position controller 90, the output unit 100, and an operation input unit 110.

The console 12 is configured as a computer comprising a processor. A controller (not shown) configured by the processor operates a program related to various types of processing or controls incorporated in a program storage memory (not shown) provided in the console 12 to realize functions of the distance measurement information acquisition unit 40, the subject posture information generation unit 50, the apparatus posture information generation unit 60, the positional relationship estimation information generation unit 70, the notification controller 80, and the apparatus position controller 90, and an imaging support information generation unit 71, an imaging position information generation unit 120, an imaging preparation comparison information generation unit 130, and an examiner posture information generation unit 140, which are described below. Also, the controller of the console 12 may perform comprehensive control of the radiography system 10 by performing control on the distance measurement device 11 and the radiography apparatus 13.

The output unit 100 of the console 12 is a display, a head-mounted display, a speaker, or the like. The output unit 100 realizes an output function of providing imaging support to a user, such as a radiologist or a doctor, according to imaging support information described below. The output unit 100 is a notification unit that is a target of the notification control, and gives notification to the user. The operation input unit 110 is a keyboard, a mouse, a microphone, a foot switch, a touch pad, a tablet, a touch pen, or the like, and receives an input operation of function settings from a user.

Figure 2:
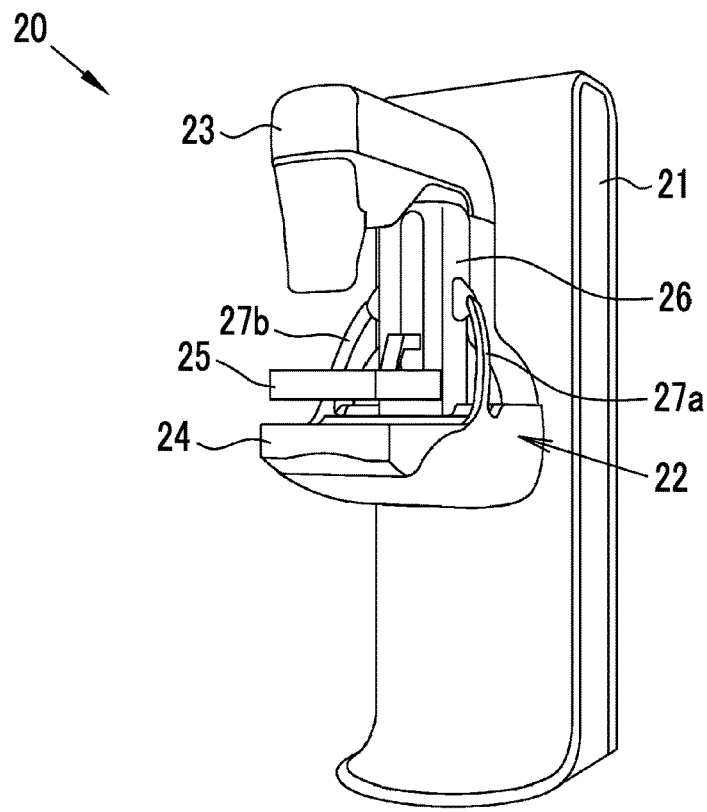
FIG. 2 is an external view of a mammography apparatus.

In the present embodiment, the radiography apparatus 13 is a mammography apparatus 20. The mammography apparatus 20 is a radiography apparatus that images a breast of a subject by using radiation, such as X-rays and gamma rays. As shown in FIG. 2, the mammography apparatus 20 comprises a stand portion 21 and a movable portion 22. The movable portion 22 comprises a radiation generation unit 23, an imaging table 24, a compression plate 25, and a raising and lowering portion 26. The movable portion 22 integrates the radiation generation unit 23 and the imaging table 24 including a radiography unit, and further is movable in a vertical direction and rotatable within a predetermined angle range while maintaining relative positions of the radiation generation unit 23 and the imaging table 24 in order to adjust an imaging position in a case in which the subject is imaged by using radiation. The stand portion 21 is a support column that supports the movable portion 22.

The radiation generation unit 23 comprises a radiation source that emits radiation toward the radiography unit. In a case in which the radiation source generates X-rays, the radiation generation unit 23 is an X-ray tube or a mono-tank in which the X-ray tube and other circuits are integrated. The radiography unit is a radiation detector that images the subject by using radiation transmitted through the subject. The radiography unit is, for example, a flat panel detector (FPD).

The imaging table 24 is a stage on which the breast of the subject is disposed, and interposes the breast of the subject with the compression plate 25 during imaging. In addition, a grip portion 27a gripped by the subject with a right hand and a grip portion 27b gripped by the subject with a left hand are attached to the imaging table 24. The grip portion 27a and the grip portion 27b are so-called arm rests. The compression plate 25 presses and flattens the breast of the subject placed on the imaging table 24. In a case in which the breast is appropriately pressed, the overlap of the mammary glands in the radiation image can be reduced, and the doctor can perform interpretation of the radiation image more appropriately. The interpretation is performed to determine the presence or absence of a lesion from the radiation image and to distinguish the lesion.

In a case in which the radiation image is captured by the mammography apparatus 20, the radiologist performs positioning of the breast of the subject and then presses the breast in order to obtain the radiation image suitable for the interpretation. The raising and lowering portion 26 raises and lowers the compression plate 25 with respect to the imaging table 24. Accordingly, the raising and lowering portion 26 supports the compression plate 25 substantially parallel to the imaging table 24.

Figure 3:
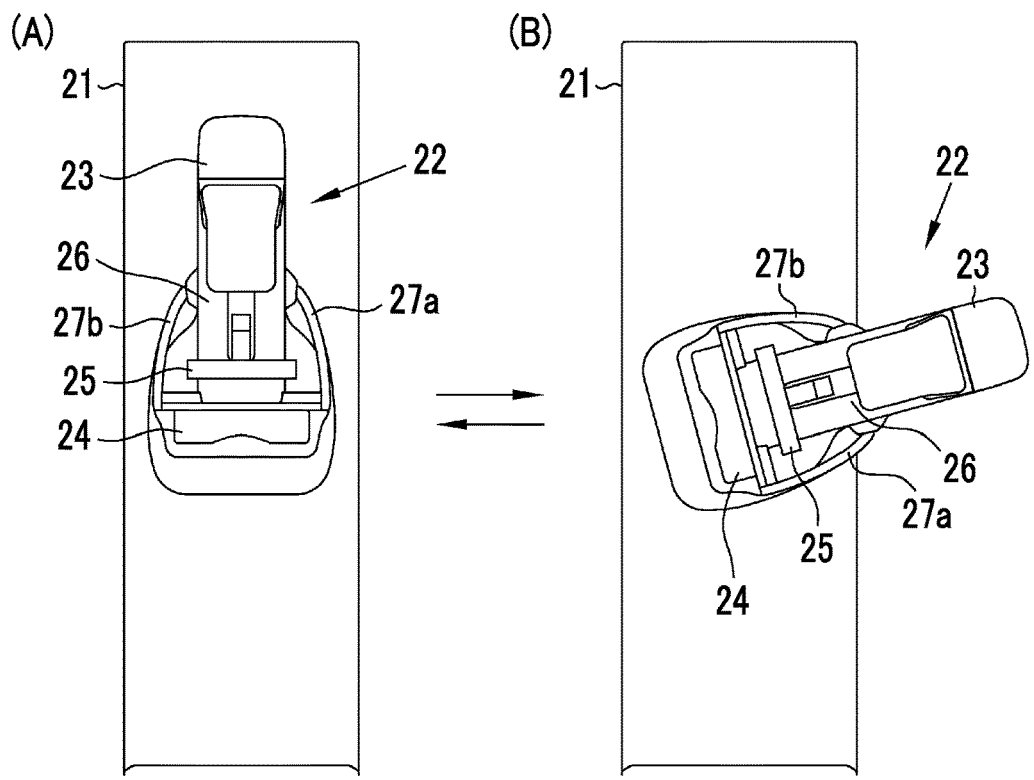
FIG. 3 is an external view showing an aspect in which a movable portion is rotated.

As shown in FIG. 3, the movable portion 22 is rotatable within the predetermined angle range while maintaining the relative positions and orientations of the radiation generation unit 23 and the imaging table 24. Therefore, the mammography apparatus 20 can dispose the imaging table 24 horizontally or dispose the imaging table 24 to be inclined from the horizontal state to perform the imaging. Specifically, as shown in a portion (A) of FIG. 3, the mammography apparatus 20 can dispose the imaging table 24 horizontally to perform cranio-caudal imaging (CC imaging) in which the breast is imaged from a cranio-caudal direction. Further, as shown in a portion (B) of FIG. 3, the mammography apparatus 20 can dispose the imaging table 24 to be inclined to perform medio-lateral oblique imaging (MLO imaging) in which the breast is imaged in a medio-lateral direction. It should be noted that, although not shown, in the mammography apparatus 20, the imaging table 24 and the like can rotate in a direction on the left side with respect to the paper surface.

Figure 4:
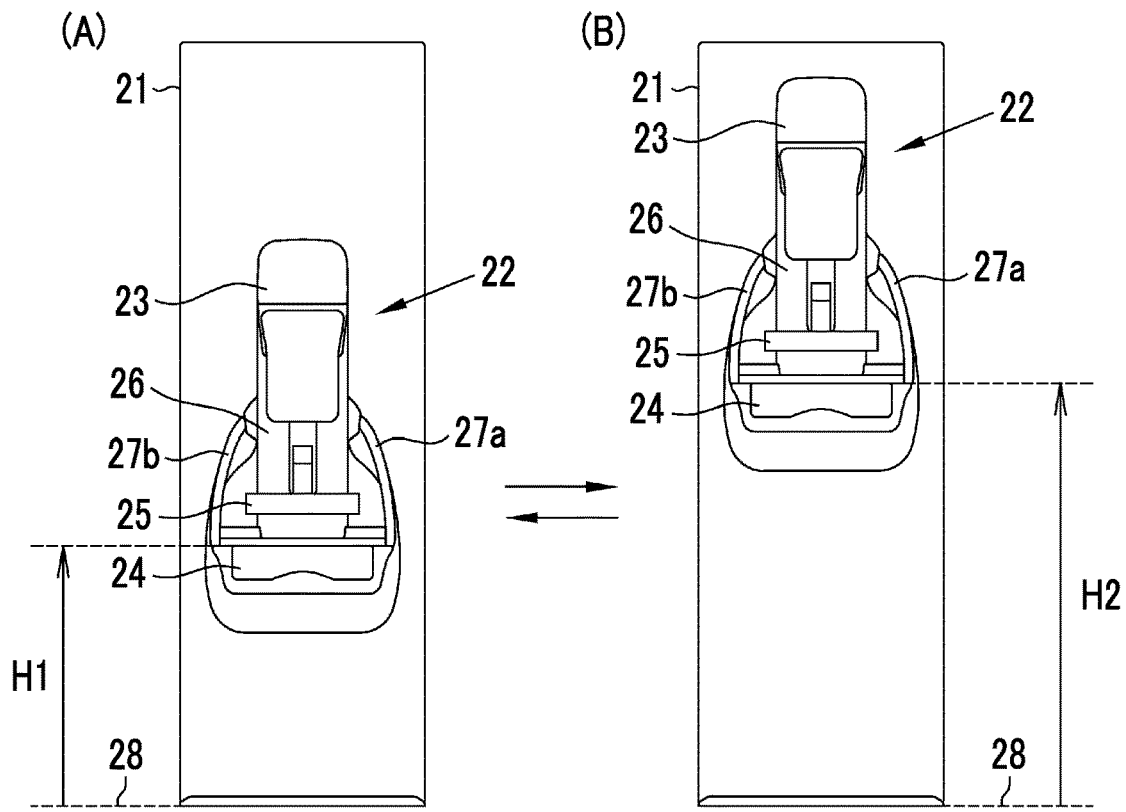
FIG. 4 is an external view showing an aspect in which a movable portion is moved in a vertical direction.

As shown in FIG. 4, the movable portion 22 is movable in the vertical direction while maintaining the relative positions and orientations of the radiation generation unit 23 and the imaging table 24. Therefore, the mammography apparatus 20 can adjust a height of the imaging table 24 by moving or rotating the movable portion 22 according to the height of the subject to perform the imaging in a reasonable posture. The height of the imaging table 24 is a height of the imaging table 24 with reference to a floor surface 28 (ground plane of the stand portion 21), and can be optionally adjusted in a range of a minimum height H1 shown in a portion (A) of FIG. 4 and a maximum height H2 shown in a portion (B) of FIG. 4 in the CC imaging. The imaging support control of adjusting the position of the imaging table 24 by moving the movable portion 22 will be described below.

The radiation emitted from the radiation generation unit 23 is transmitted through the breast of the subject, is incident on the radiography unit, and is detected to capture the radiation image. In the mammography, both the radiation image in which the right breast of the subject is imaged and the radiation image in which the left breast of the subject is imaged are usually obtained. The radiation image is transmitted to the console 12. In addition, the radiation image is transmitted to a database (not shown) connected to the console 12 by wire or wirelessly.

The database is a storage for storing the radiation image, a file server, a cloud storage, or the like. The database may be a part of a system that directly or indirectly cooperates with the radiography system 10, such as radiology information systems (RIS), hospital information systems (HIS), or picture archiving and communication systems (PACS).

The distance measurement device 11 emits the detection signal toward the detection target and receives the reflection signal from the detection target to generate the distance measurement information. In a case in which the distance measurement device 11 is installed in an examination room in which a mammography examination is performed, the detection target is, for example, the subject, the mammography apparatus, an examiner who captures the radiation image of the subject, a wall of the examination room, or an apparatus, which is installed in the examination room, other than the radiography system 10. In addition, the detection target may be a terminal that emits the reflection signal by receiving an examination signal, an integrated circuit (IC) tag that emits the reflection signal by receiving the examination signal, such as a radio frequency (RF) tag used for radio frequency identification (RFID), and the like.

Figure 5:
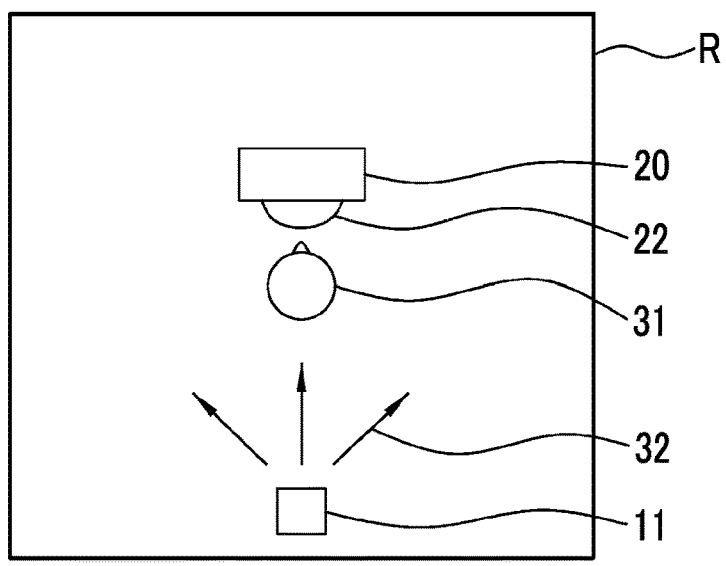
FIG. 5 is an explanatory diagram showing an example in which a distance measurement device is disposed on a back surface of a subject at a position at which a detection signal is emitted.
Figure 6:
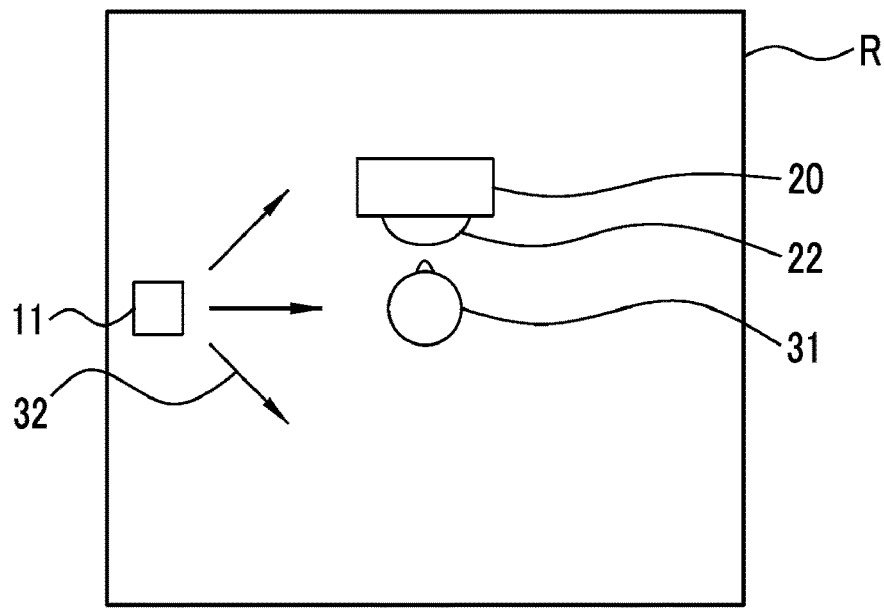
FIG. 6 is an explanatory diagram showing an example in which the distance measurement device is disposed on a side surface of the subject at the position at which the detection signal is emitted.

In the first embodiment, the distance measurement device 11 is installed at a position spaced from the mammography apparatus 20. FIGS. 5 and 6 are diagrams showing examples of a positional relationship between the distance measurement device 11, a subject 31, and the mammography apparatus 20 in a case in which an examination room R is viewed from vertically above. As shown in FIGS. 5 and 6, the distance measurement device 11 installed in the examination room R by emitting the detection signal 32 can receive the reflection signal reflected from the examination room R itself and the detection target present in the examination room R, such as the subject 31, the mammography apparatus 20, and a wall 33 of the examination room R. It should be noted that, in the present specification, the subject means a person who is the target of capturing the radiation image. In addition, the examiner means the user who is the radiologist, the doctor, or the like who captures the radiation image of the subject by operating the radiography system 10.

FIGS. 5 and 6 show the positional relationship between the subject 31 and the mammography apparatus 20, and a position at which the distance measurement device 11 is disposed in a case in which a normal mammography examination is performed in which the subject 31 stands upright to face a surface of the mammography apparatus 20 on which the movable portion 22 is positioned. It should be noted that, in FIGS. 5 and 6, a portion corresponding to the stand portion 21 is designated as the "mammography apparatus 20". In addition, a part of the detection signal 32 emitted by the distance measurement device 11 is designated by a reference numeral as a representative. A direction in which the detection signal 32 is emitted is not limited to the shown direction.

As shown in FIG. 5, the distance measurement device 11 may be disposed on a back surface of the subject 31 at a position at which the detection signal 32 is emitted. In addition, as shown in FIG. 6, the distance measurement device 11 may be disposed on a side surface of the subject 31 at the position at which the detection signal 32 is emitted. In a case in which the distance measurement device 11 is provided at a position independent of the mammography apparatus 20, it is preferable that the distance measurement device 11 is disposed at a position spaced from the subject 31 and the mammography apparatus 20, for example, on the wall surface of the examination room R. This configuration is to generate the distance measurement information from which the reflection signal is obtained from the entirety of the subject 31 and the mammography apparatus 20 to obtain an entire image of the subject 31 and the mammography apparatus 20. Also, this configuration is to reduce radio wave interference between the distance measurement device 11 and the mammography apparatus 20. It should be noted that the distance measurement device 11 may be disposed at any position of the user, but a position at which the distance measurement device 11 is not clearly recognized by the subject is preferable.

The detection signal 32 is an electromagnetic wave, such as a radio wave, a millimeter wave, or a laser beam, transmitted from a transmission unit (not shown) included in the distance measurement device 11. The transmission unit is a so-called wireless transmitter of the electromagnetic wave. The transmission unit may include an antenna that transmits the electromagnetic wave, a signal source, such as an oscillation circuit, a modulation circuit that modulates the signal, and an amplifier that amplifies the signal. In addition, the distance measurement device 11 comprises a reception unit (not shown) that receives the reflection signal. The reception unit includes an antenna that receives the reflection signal, an analog/digital (A/D) converter that converts the received reflection signal into a digital signal, and the like. The transmission unit and the reception unit of the distance measurement device 11 may be provided in one device, or the transmission unit and the reception unit may be separately installed in the examination room R.

As the distance measurement device 11, for example, a communication device that transmits and receives the electromagnetic wave of so-called Wi-Fi (registered trademark) standard, and that comprises a transmission unit that transmits the radio wave having a central frequency of 2.4 GHz or 5 GHz as the detection signal 32 and a reception unit that has a reception channel having a plurality of band widths, such as 20 MHz, 40 MHz, 80 MHz, and 160 MHz, can be applied. The distance measurement device 11 to which Wi-Fi (registered trademark) is applied can be installed at a low installation cost and can be installed regardless of the presence or absence of a shield. In a case in which Wi-Fi (registered trademark) is applied to the distance measurement device 11, the detection target is the terminal that emits the reflection signal by receiving the detection signal.

In addition, as the distance measurement device 11, a radar comprising a transmission unit that transmits a wideband radio wave having a central frequency of 1.78 GHz as the detection signal 32 and a reception unit having a T-type antenna array or the like can be applied. The distance measurement device 11 to which the radar is applied has low power and can be installed regardless of the presence or absence of a shield.

In addition, as the distance measurement device 11, a light detection and ranging or laser imaging detection and ranging (LIDAR), which transmits a laser beam, such as ultraviolet rays, visible rays, infrared rays, and near infrared rays, as the detection signal 32, can be applied. The distance measurement device 11 to which the LIDAR is applied has a high spatial resolution, and can detect a distance to the detection target that reflects the reflection signal, a shape, and a position of the detection target with high accuracy.

The distance measurement information generation unit 30 generates the distance measurement information by using the reflection signal received by the reception unit. The distance measurement information includes information on a distance from the detection target to the distance measurement device 11, information on the shape of the detection target, and information on the positional relationship between a plurality of detection targets. The generated distance measurement information is transmitted to the distance measurement information acquisition unit 40 of the console 12. The console 12 transmits the distance measurement information received by the distance measurement information acquisition unit 40 to the subject posture information generation unit 50 and the apparatus posture information generation unit 60.

The subject posture information generation unit 50 generates the subject posture information by performing analysis processing on the distance measurement information. The subject posture information is information indicating a posture of the subject in a three-dimensional space. The analysis processing of generating the subject posture information from the distance measurement information includes processing of extracting the distance measurement information on the entire body of the subject or a part of the body of the subject from the distance measurement information based on the reflection signals from all the detection targets. The generated subject posture information is transmitted to the positional relationship estimation information generation unit 70.

The subject posture information includes body axis information indicating a position of a body axis in the craniocaudal direction of the subject in a space and breast position information indicating a position of the left breast and/or the right breast of the subject in a space, which are described below. The body axis information and the breast position information are generated by the subject posture information generation unit 50.

In the first embodiment, the apparatus posture information generation unit 60 generates the apparatus posture information by performing the analysis processing on the distance measurement information. The apparatus posture information is information indicating a posture of the radiography apparatus 13 in a three-dimensional space. In the first embodiment, as shown in FIGS. 5 and 6, the distance measurement device 11 and the radiography apparatus 13 (mammography apparatus 20) are spaced from each other, and the detection target includes the radiography apparatus 13. In a case in which the apparatus posture information generation unit 60 performs the analysis processing on the distance measurement information, the analysis processing of generating the apparatus posture information from the distance measurement information includes processing of extracting the distance measurement information of the radiography apparatus from the distance measurement information of all the detection targets. The generated apparatus posture information is transmitted to the positional relationship estimation information generation unit 70.

It should be noted that, in a case in which the distance measurement device 11 and the radiography apparatus 13 are spaced from each other, information about a positional relationship between the distance measurement device 11 and the radiography apparatus 13, such as a spacing distance of the radiography apparatus 13 from the distance measurement device 11, may be input in advance by the user, and the apparatus posture information generation unit 60 may generate the apparatus posture information or assist the generation of the apparatus posture information by reading out the information.

The apparatus posture information includes movable portion position information indicating a position of the movable portion 22 in a space, which will be described below. The movable portion position information may be generated by performing the analysis processing including the processing of extracting the distance measurement information of the movable portion 22 from the distance measurement information of all the detection targets, or may be generated from the information about the positional relationship between the distance measurement device 11 and the movable portion 22, such as a spacing distance of the movable portion 22 from the distance measurement device 11, which is set in advance.

Figure 7:
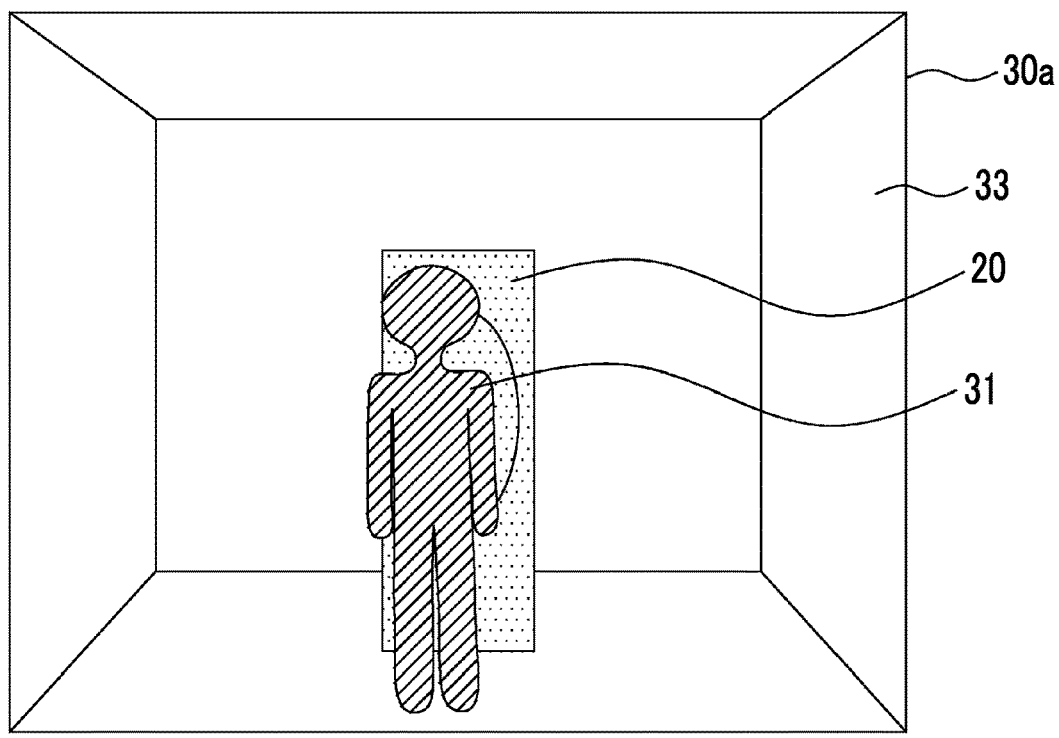
FIG. 7 is an explanatory diagram showing an example of distance measurement information generated in a case in which the distance measurement device is disposed on the back surface of the subject at the position at which the detection signal is emitted and the subject stands at a right breast imaging position.

Specific examples of the distance measurement information, the subject posture information, and the apparatus posture information will be shown. As shown in FIG. 5, in a case in which the distance measurement device 11 is disposed on the back surface of the subject 31 at the position at which the detection signal is transmitted, distance measurement information 30a including the subject 31, the mammography apparatus 20, and the wall 33 of the examination room R is generated as shown in FIG. 7. In the example of the distance measurement information 30a shown in FIG. 7, the subject 31 shown by a diagonal line is positioned closer to the distance measurement device 11 than the mammography apparatus 20 shown by a dot pattern. It should be noted that, in FIG. 7, a part of the wall 33 of the examination room R is designated by a reference numeral.

The subject posture information generation unit 50 can generate the subject posture information by extracting the subject 31 from the distance measurement information 30a as shown in FIG. 7. For example, the subject 31 can be extracted by comparing the subject 31 with a feature of a shape of a human body. In addition, the apparatus posture information generation unit 60 can generate the apparatus posture information by extracting the mammography apparatus 20 from the distance measurement information 30a as shown in FIG. 7.

In FIG. 7, the subject 31, the mammography apparatus 20, and the wall 33 of the examination room R are schematically shown. Since information on the unevenness of the surface of the mammography apparatus 20 is obtained from the distance measurement information 30a, for example, the stand portion 21, the movable portion 22, the imaging table 24, the radiation generation unit 23, and the like can be extracted by analyzing the information. In addition, the distance measurement information 30a includes information about anatomical parts, such as the head, both ears, neck, shoulders, elbows, wrists, waist, pelvis, both hips, knees, ankles, and breast, of the subject 31. Such an anatomical part that is a part of the subject's body is also called a joint point or a key point.

The subject posture information may be extracted as a position of the entire body of the subject in a space, or may be extracted as a position of a part of the body of the subject in a space. In addition, the subject posture information may be extracted as detailed subject posture information, which is generated by specifying each joint point of the subject and connecting the respective joint points.

Further, the subject posture information generation unit 50 may be a trained model to which machine learning is applied. In the machine learning, a decision tree, a support vector machine, a random forest, regression analysis, supervised learning, semi-supervised learning, unsupervised learning, reinforcement learning, deep learning, deep reinforcement learning, a neural network, a convolutional neural network, a generative adversarial network, or the like can be used. The trained model is generated by training a learning model to which the machine learning is applied. The subject posture information generation unit 50, which is the trained model, outputs the subject posture information by inputting the distance measurement information. The subject posture information generation unit 50 may be a trained model generated by applying transfer learning by using a trained model other than the subject posture information generation unit 50 trained using the teacher data, and the distance measurement information. Such a trained model is a posture estimation model that performs human posture estimation (human pose estimation) that estimates the posture of the subject by inputting distance measurement information.

Figure 8:
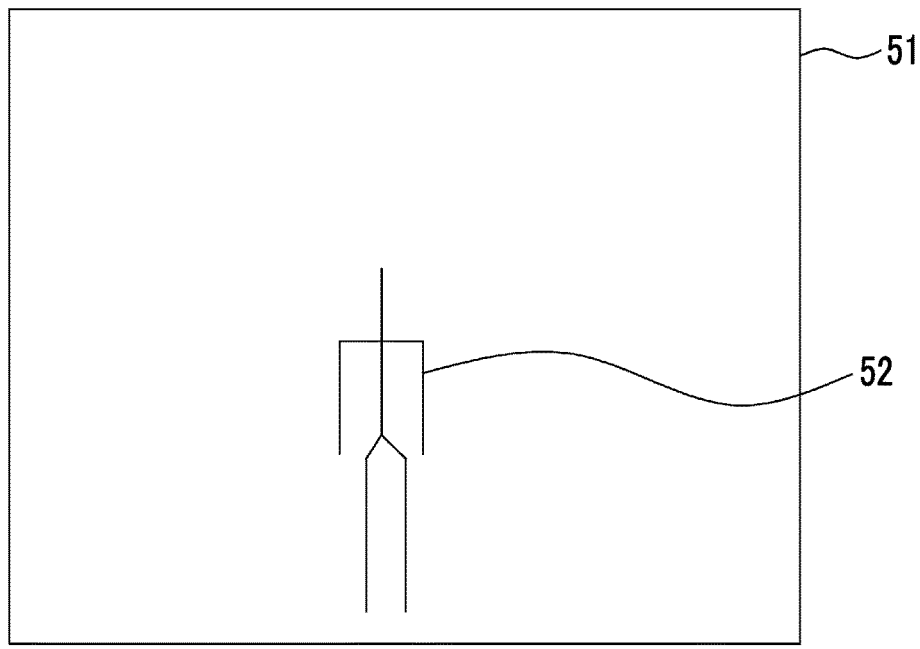
FIG. 8 is an explanatory diagram showing an example of body axis information of the subject.

In a case in which the subject posture information generation unit 50 is the trained model, for example, body axis information 52 of the subject connecting the distance measurement device 11 to the joint point of the subject 31 is output as the subject posture information 51, as shown in FIG. 8 by inputting the distance measurement information 30a as shown in FIG. 7 to the subject posture information generation unit 50. The body axis information 52 is, for example, information indicating the position of the body axis connecting the position of the head of the subject to the position of the waist.

A method of generating the subject posture information using the subject posture information generation unit 50 as the trained model is not limited to this. For example, the subject posture information can be generated by using a method described in "ZHAO, Mingmin, et al. Through-wall human pose estimation using radio signals. In: Proceedings of the IEEE Conference on Computer Vision and Pattern Recognition. 2018. p. 7356-7365.", "VASILEIADIS, Manolis; BOUGANIS, Christos-Savvas; TZOVARAS, Dimitrios. Multi-person 3D pose estimation from 3D cloud data using 3D convolutional neural networks. Computer Vision and Image Understanding, 2019, 185: 12-23.", "JIANG Wenjun, et al. Towards 3D human pose construction using WiFi. In: Proceedings of the 26th Annual International Conference on Mobile Computing and Networking. 2020. p. 1-14.", or "WANG Fei, et al. Person-in-WiFi: Fine-grained person perception using WiFi. In: Proceedings of the IEEE/CVF International Conference on Computer Vision. 2019. p. 5452-5461.".

In addition, the apparatus posture information may be extracted as a position of the entire mammography apparatus in a space, or may be extracted as a position of a part of the mammography apparatus in a space. In addition, the apparatus posture information may be extracted as detailed posture information of the entire mammography apparatus generated by specifying the components, such as the stand portion 21, the movable portion 22, the imaging table 24, and the radiation generation unit 23, constituting the mammography apparatus as the key points and connecting a plurality of key points.

Figure 9:
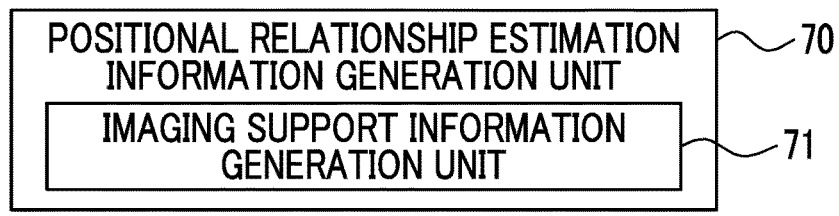
FIG. 9 is a block diagram showing a function of a positional relationship estimation information generation unit.

The positional relationship estimation information generation unit 70 generates the positional relationship estimation information based on the subject posture information and the apparatus posture information. The positional relationship estimation information is information indicating the position, the posture, and/or the orientation of the subject with respect to the radiography apparatus 13, and is information indicating what position, posture, or orientation the subject has with respect to the radiography apparatus 13. In addition, as shown in FIG. 9, the imaging support information generation unit 71 provided in the positional relationship estimation information generation unit 70 generates the imaging support information. The imaging support information includes notification control information for instructing the output unit 100 to perform the notification control of giving notification about the imaging of the radiation image, and imaging apparatus control information for giving an instruction to perform the imaging apparatus control with respect to the radiography apparatus 13.

Specific examples of the positional relationship estimation information and the imaging support information will be described. For example, in a case in which the console 12 acquires the distance measurement information 30a shown in FIG. 7, the positional relationship estimation information generation unit 70 generates, based on the subject posture information and the apparatus posture information, the positional relationship estimation information indicating that the subject 31 faces a direction in which the movable portion 22 of the mammography apparatus 20 is positioned, and also indicating that the subject 31 is in an upright standing posture on the left side of the mammography apparatus 20, that is, at a position (right breast imaging position) at which the right breast of the subject is imaged, as viewed from the distance measurement device 11. In this case, the imaging support information generation unit 71 uses the positional relationship estimation information to generate the notification control information for giving an instruction to give notification that the subject stands at the right breast imaging position.

The positional relationship estimation information on the orientation of the subject 31 with respect to the radiography apparatus 13 indicating that "The subject 31 faces the direction in which the movable portion 22 of the mammography apparatus 20 is positioned" may be generated from the subject posture information indicating the position of a part of the face of the subject 31, such as eyes or nose, and the apparatus posture information, or may be generated from the subject posture information generated based on the distance measurement information indicating the IC tag attached to examination clothes worn by the subject, and the apparatus posture information.

The positional relationship estimation information on the position of the subject 31 with respect to the radiography apparatus 13 indicating that "the subject 31 is positioned at the right breast imaging position or a position (left breast imaging position) at which the left breast of the subject is imaged" may be generated from the subject posture information indicating the position of the head of the subject 31 and the apparatus posture information. In addition, the positional relationship estimation information may be generated from the subject posture information, which is generated based on the distance measurement information indicating the IC tag attached to the examination clothes worn by the subject, and the apparatus posture information.

It should be noted that, as the positional relationship estimation information, the positional relationship estimation information may be generated, which indicates whether or not the subject is positioned at a position at which the radiation image can be captured with the assistance of the examiner in the normal mammography examination, that is, indicating that the subject is positioned at a position close to the mammography apparatus 20 to the extent that the breast can be pressed with the compression plate 25 or the subject is positioned at a position far from the mammography apparatus 20 at which the breast cannot be pressed by the compression plate 25. In addition, the positional relationship estimation information generation unit 70 may be set in advance so as not to generate the positional relationship estimation information indicating that the subject is positioned at the right breast imaging position or the left breast imaging position in a case in which the subject and the position of the mammography apparatus 20 are far from each other.

The positional relationship estimation information on the posture of the subject 31 with respect to the radiography apparatus 13 indicating that "The subject is in an upright standing posture" may be generated from the subject posture information generated by connecting the joint points of the subject 31. In addition, the positional relationship estimation information may be generated from the subject posture information, which is generated based on the distance measurement information indicating a plurality of IC tags attached to the neck peripheral portions and waist peripheral portions of the examination clothes worn by the subject, and the apparatus posture information.

The positional relationship estimation information generation unit 70 may generate any one of the positional relationship estimation information on the orientation of the subject 31 with respect to the radiography apparatus 13, the positional relationship estimation information on the position of the subject 31 with respect to the radiography apparatus 13, or the positional relationship estimation information on the posture of the subject 31 with respect to the radiography apparatus 13, may generate any plurality of the positional relationship estimation information, or may generate all the positional relationship estimation information. The imaging support information generation unit 71 generates the imaging support information by using any of the positional relationship estimation information.

Figure 10:
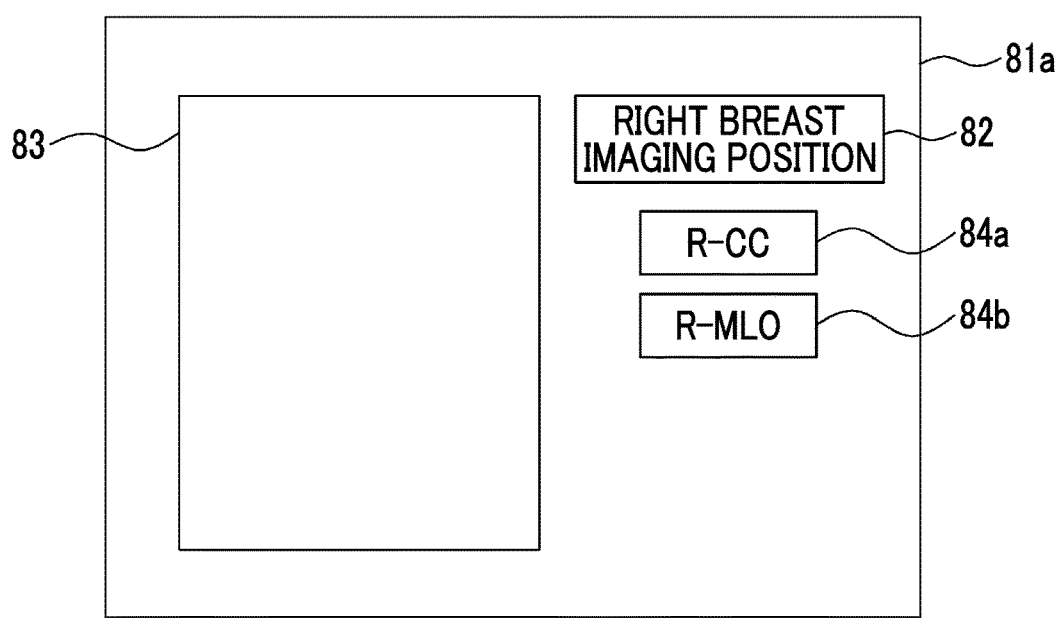
FIG. 10 is an image diagram showing an example of an imaging support image for giving notification that a position of the subject is the right breast imaging position.

The notification control information generated by the imaging support information generation unit 71 is transmitted to the notification controller 80. The notification controller 80 performs the notification control of generating an imaging support image 81a as shown in FIG. 10 which gives notification that the subject stands at the position at which any of the breasts is imaged, and displaying the imaging support image 81a on a display which is the output unit 100. By checking the imaging support image 81a displayed on the display, the user can check the radiation image to be captured. As a result, it is possible to prevent the user from making a mistake, such as duplication imaging of the left and right breasts, and to suppress the exposure of the subject.

In the example of the imaging support image 81a shown in FIG. 10, an imaging support information display field 82 is provided. In the example shown in FIG. 10, in the imaging support information display field 82, "right breast imaging position" is displayed in order to give notification that the subject stands at the right breast imaging position. The imaging support image 81a may be provided with a radiation image display field 83 for displaying the radiation image to be captured. Also, information about the examination, such as a date and a patient name, may be displayed on the imaging support image 81a.

In addition, the notification controller 80 may display a graphical user interface (GUI) that gives an instruction to perform the imaging of the CC imaging or the MLO imaging on the imaging support image according to the received notification control information. That is, the imaging apparatus control can be performed with respect to the radiography apparatus 13 by operating the GUI displayed on the imaging support image.

In the example of the imaging support image 81a shown in FIG. 10, in a case in which the notification control information for giving notification that the subject stands at the right breast imaging position is received, an imaging instruction control button 84a, which is displayed as "R-CC", for instructing the mammography apparatus 20 to perform the CC imaging of the right breast and an imaging instruction control button 84b, which is displayed as "R-MLO", for instructing the mammography apparatus 20 to perform the MLO imaging of the right breast are displayed as the GUI. In this case, for example, the movable portion 22 moves in the vertical direction by the user operating the imaging instruction control button 84a for instructing the mammography apparatus 20 to perform the CC imaging of the right breast. In addition, the movable portion 22 rotates by the user operating the imaging instruction control button 84b for instructing the mammography apparatus 20 to perform the MLO imaging of the right breast.

By performing such control, it is possible to prompt the user to select whether to execute the CC imaging or the MLO imaging on the right breast or the left breast according to the position of the subject with respect to the mammography apparatus. As a result, it is possible to support smooth capturing of the radiation image. It should be noted that, in this case, by using the breast position information included in the subject posture information, the imaging apparatus control of moving or rotating the movable portion 22 according to the position of the breast of the subject indicated by the breast position information may be performed.

It should be noted that the positional relationship estimation information generation unit 70 may generate the positional relationship estimation information indicating a rotation angle of the movable portion 22 with respect to the subject from the subject posture information and the information on the position or the shape of the movable portion 22 included in the apparatus posture information. In this case, the imaging support information generation unit 71 may determine to perform the CC imaging or the MLO imaging by using the positional relationship estimation information indicating the rotation angle of the movable portion 22 with respect to the subject, generate the result as the imaging support information, and transmit the generated imaging support information to the notification controller 80 or the apparatus position controller 90. The notification controller 80 may perform control of displaying that the CC imaging or the MLO imaging is performed in the imaging support information display field 82 of the imaging support image 81a. For example, in a case in which the subject stands at the position at which the CC imaging of the right breast is performed, the notification control of displaying "R-CC" in the imaging support information display field 82 may be performed.

Figure 11:
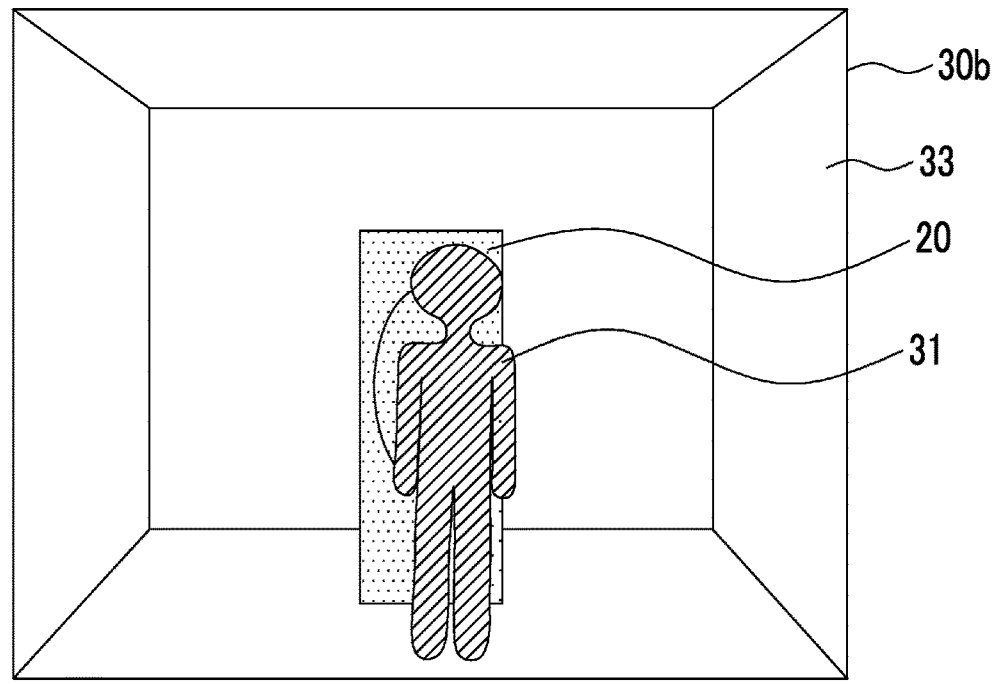
FIG. 11 is an explanatory diagram showing an example of distance measurement information generated in a case in which the distance measurement device is disposed on the back surface of the subject at the position at which the detection signal is emitted and the subject stands at a left breast imaging position.

Other specific examples of the positional relationship estimation information and the imaging support information will be described. For example, the console 12 acquires distance measurement information 30b as shown in FIG. 11. In this case, the positional relationship estimation information generation unit 70 generates, based on the subject posture information and the apparatus posture information, the positional relationship estimation information indicating that the subject 31 faces the direction in which the movable portion 22 of the mammography apparatus 20 is positioned, and also indicating that the subject 31 in an upright standing posture on the right side of the mammography apparatus 20, that is, at the left breast imaging position, as viewed from the distance measurement device 11. In this case, the imaging support information generation unit 71 uses the positional relationship estimation information to generate the notification control information for giving an instruction to give notification that the subject stands at the left breast imaging position, and transmits the generated notification control information to the notification controller 80.

Figure 12:
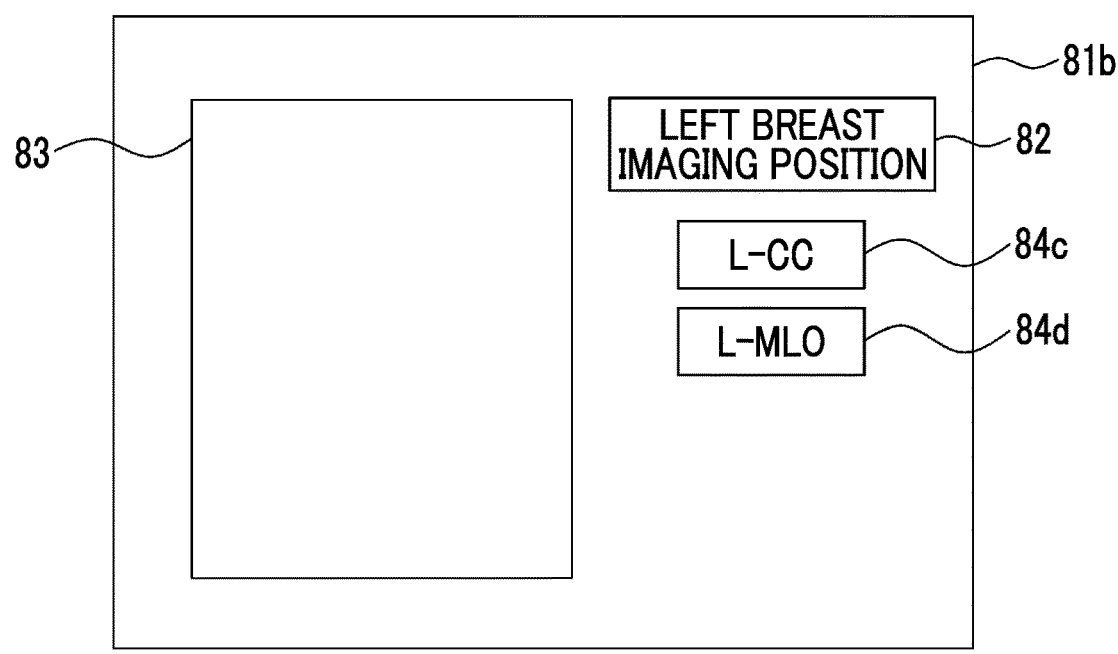
FIG. 12 is an image diagram showing an example of an imaging support image for giving notification that a position of the subject is the left breast imaging position.

In this case, the notification controller 80 performs the control of generating an imaging support image 81b as shown in FIG. 12 which gives notification that the subject stands at the left breast imaging position, and displaying the imaging support image 81 on the display which is the output unit 100. In the example of the imaging support image 81b shown in FIG. 12, "left breast imaging position" is displayed in the imaging support information display field 82. In addition, in FIG. 12, an imaging instruction control button 84c, which is displayed as "L-CC", for instructing the mammography apparatus 20 to perform the CC imaging of the left breast and an imaging instruction control button 84d, which is displayed as "L-MLO", for instructing the mammography apparatus 20 to perform the MLO imaging of the left breast may be displayed as the GUI.

In addition, in a case in which the distance measurement device 11 is disposed on the side surface of the subject 31 at the position at which the detection signal 32 is emitted, as shown in FIG. 6, the console 12 acquires the distance measurement information shown in FIG. 13 or FIG. 14, for example. In a case in which the console 12 acquires distance measurement information 30c shown in FIG. 13, the positional relationship estimation information generation unit 70 determines, based on the subject posture information and the apparatus posture information, that the subject 31 faces a direction in which the movable portion 22 of the mammography apparatus 20 is positioned, and also that the subject 31 stands on the front side with respect to the mammography apparatus 20, that is, at the right breast imaging position, as viewed from the distance measurement device 11. In this case, the positional relationship estimation information indicating that the subject is in an upright standing posture at the position at which the right breast is imaged by the CC imaging is generated. In this case, the imaging support information generation unit 71 performs the notification control of generating the notification control information by using the positional relationship estimation information, and displaying, on the display, the imaging support image 81a displayed as "right breast imaging position" on the imaging support information display field 82 as shown in FIG. 10.

In a case in which the console 12 acquires distance measurement information 30d shown in FIG. 14, the positional relationship estimation information generation unit 70 generates, based on the subject posture information and the apparatus posture information, the positional relationship estimation information indicating that the subject 31 faces a direction in which the movable portion 22 of the mammography apparatus 20 is positioned, and also indicating that the subject 31 in an upright standing posture on the back side with respect to the mammography apparatus 20, that is, at the left breast imaging position, as viewed from the distance measurement device 11. In this case, the imaging support information generation unit 71 generates the notification control information by using the positional relationship estimation information. In this case, in order to give notification that the subject stands at the position at which the left breast is imaged by the CC imaging, for example, the notification control of displaying, on the display, the imaging support image 81b displayed as "left breast imaging position" on the imaging support information display field 82, as shown in FIG. 12. It should be noted that FIG. 13 or FIG. 14 depicts an auxiliary line 34 for making it easy to understand whether the subject 31 stands on the back side or the front side as viewed from the distance measurement device 11. The auxiliary line 34 is not included in the distance measurement information 30c and 30d.

It should be noted that the example of the notification control is not limited to this. For example, a voice message may be used to give notification that the right breast and/or the left breast of the subject is to be imaged. In addition, a lamp that emits light of different colors depending on the notification about the imaging of the right breast and the notification about the imaging of the left breast may be provided in the output unit 100, and the notification may be performed according to the color of the light emitted by the lamp.

In addition, the breast position information indicating the position of the right breast and/or the left breast of the subject may be generated as the subject posture information. In this case, the movable portion position information indicating the position of the movable portion 22 is generated as the apparatus posture information. In this case, the positional relationship estimation information generation unit 70 may generate the imaging apparatus control information for giving an instruction of the imaging apparatus control of moving or rotating the movable portion 22 according to the position of the right breast or the left breast of the subject from the positional relationship between the right breast and/or the left breast of the subject and the movable portion 22 based on the subject posture information and the apparatus posture information. The imaging apparatus control information is transmitted to the apparatus position controller 90.

The apparatus position controller 90 performs control of moving or rotating the movable portion 22 with respect to the mammography apparatus 20 based on the imaging apparatus control information. For example, for the CC imaging, the imaging apparatus control of moving the movable portion 22 in the vertical direction to a position at which the imaging table 24 matches a lower edge of the breast of the subject is performed. In addition, for the MLO imaging, the imaging apparatus control of rotating the movable portion 22 according to the position of the breast of the subject may be performed.

The example in which the imaging apparatus control of moving or rotating the movable portion 22 according to the position of the right breast or the left breast of the subject is performed is particularly suitable in a case in which the distance measurement device 11 is disposed at the position at which the examination signal is emitted to the side surface of the subject and the distance measurement information as shown in FIG. 13 or FIG. 14 can be generated.

The position of the movable portion 22 is decided by using the breast position information and the movable portion position information, and the imaging apparatus control of automatically moving the movable portion 22 is performed, so that the capturing of the radiation image can be supported by saving the trouble of moving the movable portion 22 by setting by the user.

Unlike a camera that captures an image, the distance measurement device 11 that transmits and receives the electromagnetic wave does not have a resolution to the extent that the subject can be specified, so that the privacy of the subject can be protected. Since the mammography examination is an examination in which the breast is imaged, even for the purpose of specifying the position of the subject, the fact that the camera is installed in the examination room imposes a psychological burden on the subject, and there is a possibility that the radiation image cannot be captured smoothly. Therefore, by using the distance measurement device 11, it is possible to acquire an accurate position of the subject and provide the imaging support without installing the camera in the examination room.

In addition, while the distance measurement information acquired by the distance measurement device 11 does not have a resolution as that of the image captured by the camera, it is possible to obtain highly accurate information on the distance from the detection target to the distance measurement device 11, the shape of the detection target, each position of the plurality of detection targets, and the like. Therefore, by using the distance measurement information, it is possible to perform highly accurate control of the radiography apparatus 13 without performing advanced image processing. In addition, it is possible to give notification about the capturing of the radiation image by using highly accurate information regarding the positional relationship between the subject and the radiography apparatus.

Further, in a case in which the distance measurement information is obtained by using the distance measurement device 11, even in a case in which it is difficult to obtain the position information of the subject, the radiography apparatus, and the like from the camera image, such as in a situation in which the examination room is dark or in a situation in which many objects are disposed in the examination room, it is possible to obtain accurate position information of the subject, the radiography apparatus, and the like.

It should be noted that, it is preferable that the distance measurement information acquired by the console 12 is associated with time-series information. In this case, the subject posture information generation unit 50 generates the subject posture information in which the joint points of the subject and information on a time when the joint points are specified are associated with each other. The subject posture information generation unit 50 transmits the subject posture information in which the joint points of the subject and the information on the time are associated with each other to the positional relationship estimation information generation unit 70. The positional relationship estimation information generation unit 70 may generate the positional relationship estimation information indicating the posture and/or the orientation of the subject with respect to the radiography apparatus 13 based on a temporal change of the joint points of the subject by using the subject posture information at a plurality of time points. Also, the positional relationship estimation information indicating the position of the subject with respect to the radiography apparatus 13 at the current time point may be generated. With the configuration described above, the information indicating what position, posture, or orientation the subject has with respect to the radiography apparatus 13 can be obtained from the temporal change of the joint points of the subject based on the distance measurement information without obtaining a moving image in which the camera images are continuously connected in a time series.

In a case of in which the positional relationship estimation information indicating that the subject is positioned at the right breast imaging position or the left breast imaging position is generated, it may be determined whether the position of the body axis in the cranio-caudal direction of the subject is the right breast imaging position or the left breast imaging position by using the body axis information as the subject posture information.

In this case, as shown in FIG. 15, the imaging position information generation unit 120 is provided in the imaging support information generation unit 71, and the imaging position information generation unit 120 uses the body axis information and the apparatus posture information to generate the imaging position information which is a result of determination as to whether the position of the body axis in the cranio-caudal direction of the subject is the right breast imaging position or the left breast imaging position. The positional relationship estimation information generation unit 70 generates the imaging position information as the positional relationship estimation information. In this case, the imaging position information is the positional relationship estimation information indicating the position of the subject with respect to the mammography apparatus. In this case, the imaging support information generation unit 71 generates the notification control information and/or the imaging apparatus control information based on the imaging position information. Hereinafter, the "breast imaging position" will be used as a term that collectively represents the right breast imaging position and the left breast imaging position.

Figure 16:
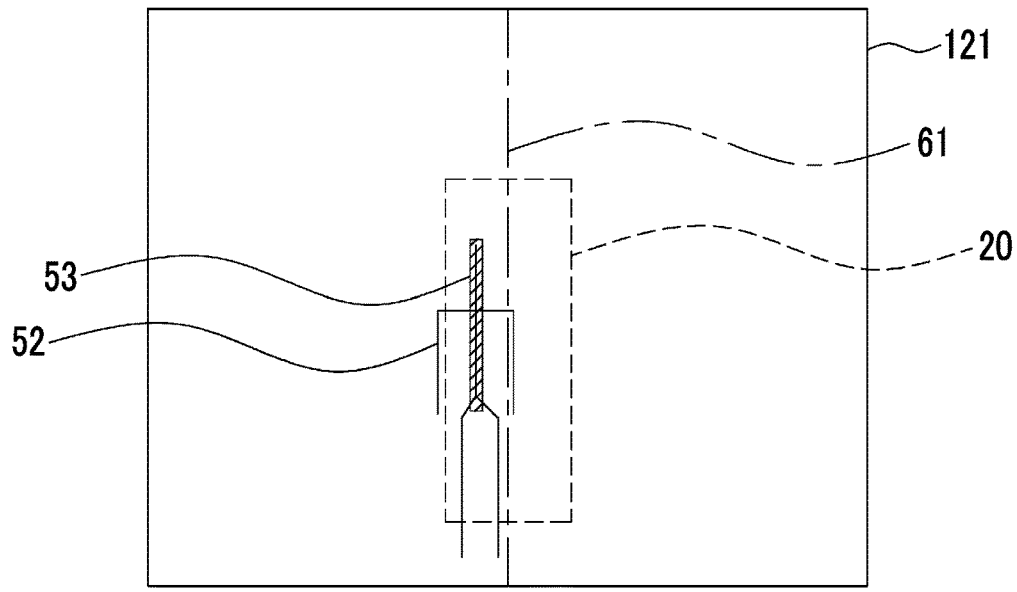
FIG. 16 is an explanatory diagram showing an example of a generation method of imaging position information.

A specific example of the generation of the imaging position information will be described with reference to FIG. 16. FIG. 16 is a diagram showing an example of information 121 used for the generation of the imaging position information in the imaging position information generation unit 120 in a case in which the console 12 acquires the distance measurement information 30*a* as shown in FIG. 7. The imaging position information generation unit 120 receives, as the subject posture information, the body axis information 52 indicating the position of the body axis in the cranio-caudal direction (body axis in the vertical direction) of the subject as shown in FIG. 16. Also, as shown in FIG. 16, the apparatus posture information indicating the position of the mammography apparatus 20 is received.

The imaging position information generation unit 120 compares the positional relationship between a position of a trunk axis 53 of the subject included in the body axis information 52 and a position of a central axis 61 in the vertical direction of the mammography apparatus 20 included in the apparatus posture information. In FIG. 16, since the position of the trunk axis 53 of the subject is positioned on the left side of the central axis 61 in the vertical direction of the mammography apparatus 20 as viewed from the distance measurement device 11, the imaging position information generation unit 120 determines that the breast imaging position is the right breast imaging position, and generates the determination result as the imaging position information. It should be noted that, in a case in which the apparatus posture information is the information input in advance, it is preferable that the position of the central axis 61 in the vertical direction of the mammography apparatus 20 is information calculated by using the apparatus posture information.

It should be noted that the imaging position information may be generated by a method other than the comparison of the body axis. For example, in a case in which the console 12 acquires the distance measurement information 30a as shown in FIG. 7, a difference may be calculated by specifying a position of a left end of the subject 31 and a position of a left end of the mammography apparatus 20, and the breast imaging position may be determined according to the magnitude of the difference to generate the imaging position information. However, in this case, there is a possibility that correct imaging position information cannot be generated depending on a body shape of the subject. Therefore, by using the body axis information including the position of the trunk axis 53 of the subject, it is possible to accurately determine the standing position of the subject regardless of the body shape of the subject.

In a case in which the imaging position information is generated, the imaging support information generation unit 71 generates the notification control information for giving notification that the subject is positioned at the right breast imaging position or the left breast imaging position based on the imaging position information, and transmits the generated notification control information to the notification controller 80. The notification controller 80 performs control of generating the imaging support images 81a and 81b as shown in FIG. 10 or FIG. 12 and displaying the generated imaging support images 81a and 81b on the display. It should be noted that the notification method is not limited to the display of the imaging support image. For example, the notification may be performed by the voice message from the speaker as the output unit 100, or the notification may be performed by an emission color or an emission pattern of the lamp as the output unit 100.

In addition, the imaging support information generation unit 71 may generate imaging preparation comparison information as a result of a comparison between the imaging position information and the imaging preparation information input to the console 12 in advance, and may generate the notification control information or the imaging apparatus control information based on the imaging preparation comparison information. The imaging preparation information is information for giving an instruction to capture the radiation image of whether the right breast or the left breast of the subject. The imaging position information is input to the console 12 by the user via the operation input unit 110. Further, the imaging position information may be transmitted to the console 12 from a device having a function of receiving and transmitting an imaging order.

Figure 17:
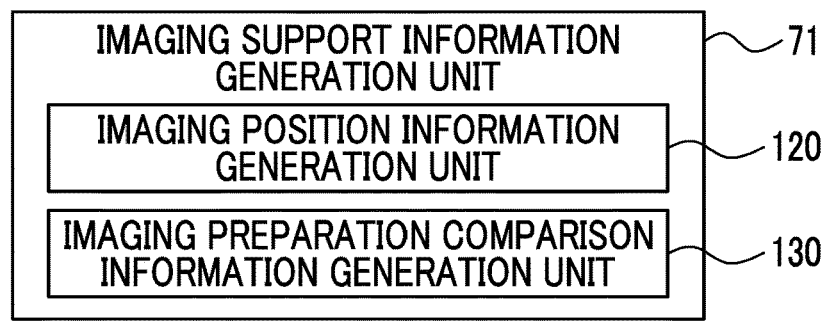
FIG. 17 is a block diagram showing a function of a imaging preparation comparison information generation unit.

In this case, as shown in FIG. 17, the positional relationship estimation information generation unit 70 is provided with the imaging preparation comparison information generation unit 130 in addition to the imaging position information generation unit 120. The imaging preparation comparison information generation unit 130 compares the imaging position information generated by the imaging position information generation unit 120 with the imaging preparation information input to the console 12, and generates the imaging preparation comparison information as the comparison result. That is, the imaging preparation comparison information generation unit 130 compares whether or not the breast that is set in advance as the imaging target of the radiation image indicated as the imaging preparation information matches the breast that is used as the imaging target of the radiation image by the subject indicated by the imaging position information.

For example, the imaging position information indicating the breast imaging position is the left breast imaging position is generated in a state in which the instruction to capture the radiation image of the right breast is input in advance as the imaging preparation information. In this case, the imaging preparation comparison information generation unit 130 generates the imaging preparation comparison information indicating that the breast (right breast) that is set in advance as the imaging target of the radiation image does not match the breast (left breast) that is used as the imaging target of the radiation image by the subject.

The imaging support information generation unit 71 generates, based on the imaging preparation comparison information, the notification control information for giving notification that the breast that is set in advance as the imaging target of the radiation image match or does not match the breast that is used as the imaging target of the radiation image by the subject, and transmits the generated notification control information to the notification controller 80.

Hereinafter, examples of the notification control and the imaging apparatus control in a case in which the notification control information for giving notification that the breast that is set in advance as the imaging target of the radiation image does not match the breast that is set as the imaging target of the radiation image by the subject is generated will be described.

Figure 18:
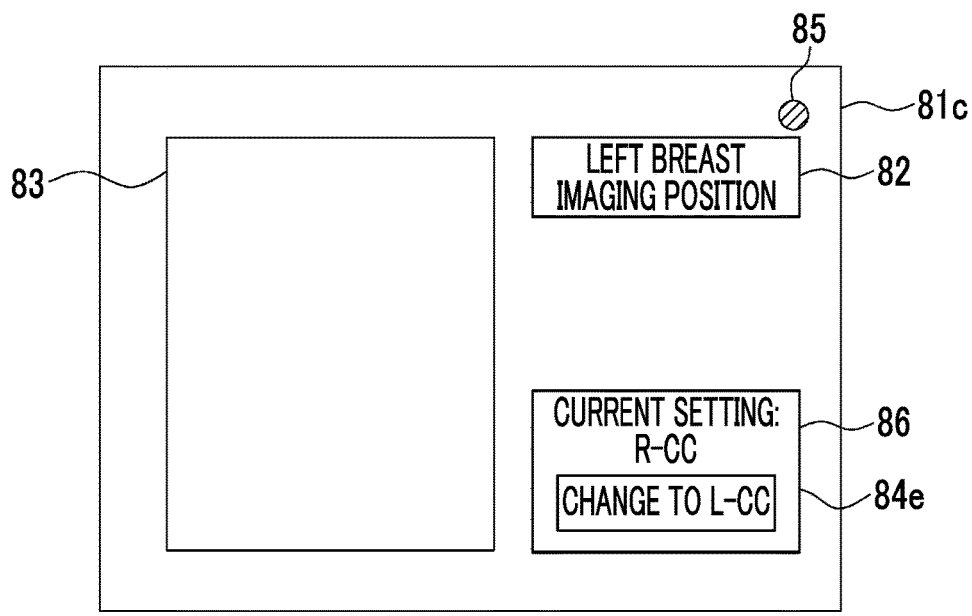
FIG. 18 is an image diagram showing an example of an imaging support image for giving notification that a breast that is set in advance as an imaging target of a radiation image does not match a breast that is used as the imaging target of the radiation image by the subject.

The breast that is set in advance as the imaging target of the radiation image (breast indicated as the imaging preparation information) is the right breast, and the breast that is used as the imaging target of the radiation image by the subject (breast indicated as the imaging position information) is the left breast. In this case, for example, the notification controller 80 performs notification control of generating an imaging support image 81c as shown in FIG. 18 and displaying the generated imaging support image 81c on the display. In the example of the imaging support image 81c shown in FIG. 18, "left breast imaging position" is displayed in the imaging support information display field 82, which indicates that the subject stands at the left breast imaging position. Further, in the example of the imaging support image 81c shown in FIG. 18, a warning display mark 85 for giving notification that the breast as a target for notification in the imaging support information display field 82 does not match the breast indicated as the imaging preparation information is displayed. The notification method is not limited to this, and the notification may be given by the text message in the imaging support image or the voice message emitted from the speaker, such as "It does not match imaging preparation information" or "Please move subject to right breast imaging position".

Further, in the imaging support image, an imaging instruction control button 84e for instructing the mammography apparatus 20 to perform the imaging of the breast on the opposite side of the breast that is set in advance as the imaging target of the radiation image indicated as the imaging preparation information in order to match the imaging position information may be displayed as the GUI. In the example of the imaging support image 81*c* shown in FIG. 18, the fact that the instruction to perform the CC imaging of the right breast is given in advance is indicated by displaying "current setting: R-CC" in an imaging preparation information display field 86. In addition, in the imaging support image 81*c* in the example shown in FIG. 18, the imaging instruction control button 84*e* for instructing the mammography apparatus 20 to perform the CC imaging of the left breast is displayed according to the display of "left breast imaging position" in the imaging support information display field 82.

By performing such notification control, in a case in which the imaging preparation comparison information input in advance by the user or input as the imaging order is different from the actual position of the subject, the user can change the breast for which the radiation image is captured, according to the position at which the subject stands.

In addition, in a case in which the imaging preparation comparison information indicating that the breast for which the instruction to capture the radiation image is given does not match the breast intended by the subject to capture the radiation image is generated, the imaging support information generation unit 71 may generate the imaging apparatus control information for moving or rotating the movable portion 22. In this case, the apparatus position controller 90 can perform the imaging apparatus control of changing the rotation direction of the movable portion 22 to an opposite orientation, for example. By performing such imaging apparatus control, for example, in a case in which an instruction to perform the MLO imaging of the right breast is input in advance as the imaging preparation information, the MLO imaging of the left breast can be performed.

It should be noted that, in a case in which the imaging preparation comparison information indicating that the breast that is set in advance as the imaging target of the radiation image matches the breast that is used by the subject as the imaging target of the radiation image is generated, in the imaging support image 81*c* shown in FIG. 18, the notification control of hiding the warning display mark 85 may be performed. Further, a mark indicating that the breast for which the instruction to capture the radiation image is given matches the breast intended by the subject to capture the radiation image may be displayed on the imaging support image. Further, the GUI for giving an instruction to execute the imaging as set in advance may be displayed on the imaging support image. With the configuration described above, it is possible to notify the user that the imaging can be performed according to the imaging preparation information input in advance, or to execute the imaging.

The positional relationship estimation information generation unit 70 may generate the positional relationship estimation information indicating the position of the left breast or the right breast of the subject with respect to the movable portion based on the breast position information included in the subject posture information and the movable portion position information included in the apparatus posture information. In this case, in a case in which a distance between the position of the breast of the subject and the position of the movable portion 22 is equal to or greater than a specific distance based on the positional relationship estimation information, the imaging support information generation unit 71 may generate the notification control information for giving notification of that fact. In this case, in a case in which a specific imaging distance is determined in advance for the distance between the position of the breast of the subject indicated by the breast position information and the position of the movable portion 22 indicated by the movable portion position information, and the distance between the position of the breast of the subject and the position of the movable portion 22 is equal to or greater than the specific imaging distance, the notification control information is generated. It should be noted that the "position of the movable portion 22" indicated by the movable portion position information may be the "position of the imaging table 24".

Figure 19:
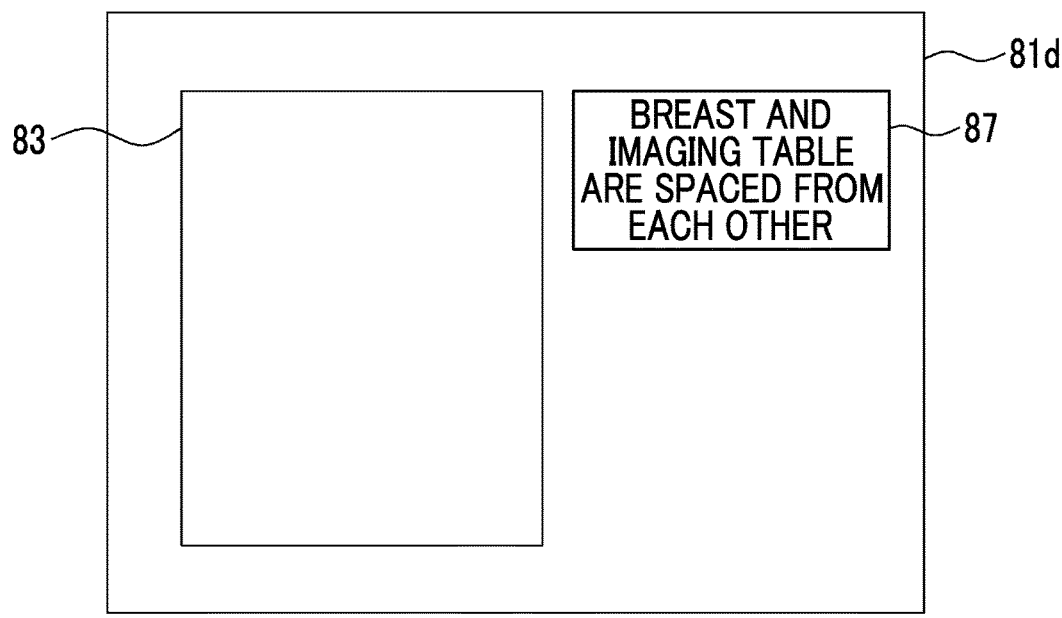
FIG. 19 is an image diagram showing an example of an imaging support image for giving notification that a distance between a position of the breast of the subject and a position of the movable portion is equal to or greater than a specific imaging distance.

The notification controller 80 that receives such notification control information performs the notification control of generating an imaging support image 81*d* shown in FIG. 19, for giving notification that the distance between the position of the breast of the subject and the position of the movable portion 22 are equal to or greater than the specific imaging distance, and displaying the generated imaging support image 81*d* on the display. In the example of the imaging support image 81*d* shown in FIG. 19, a text message 87 of "The breast and the imaging table are spaced from each other" is displayed. In addition, instead of the text message or together with the text message, the notification control of giving notification that the distance between the position of the breast of the subject and the position of the movable portion 22 is equal to or greater than the specific imaging distance may be performed by a voice message. With the configuration described above, it is possible to detect the position of the breast of the subject and prompt the user to check whether or not the height of the movable portion 22, particularly the imaging table 24, is extremely deviated.

It should be noted that the specific imaging distance may be a value optionally determined by the user and input to the console 12 or may be an automatically set value. The example in which the notification is performed in a case in which the distance between the position of the breast of the subject and the position of the movable portion 22 is equal to or greater than the specific imaging distance is suitable in a case in which the distance measurement device 11 is disposed at a position at which the distance measurement information as shown in FIG. 13 or FIG. 14 can be generated.

In addition, in a case in which the positional relationship estimation information generation unit 70 generates the positional relationship estimation information indicating the position of the left breast or the right breast of the subject with respect to the movable portion, the imaging support information generation unit 71 may generate the imaging apparatus control information for performing control of moving or rotating the movable portion 22 based on the positional relationship estimation information. In this case, the apparatus position controller 90 that receives the apparatus control information performs control of moving or rotating the movable portion 22 with respect to the mammography apparatus 20 based on the imaging apparatus control information. For example, for the CC imaging, the imaging apparatus control of moving the movable portion 22 in the vertical direction to a position at which the imaging table 24 matches a lower edge of the breast of the subject is performed. In addition, for the MLO imaging, the imaging apparatus control of rotating the movable portion 22 according to the position of the breast of the subject may be performed.

Figure 20:
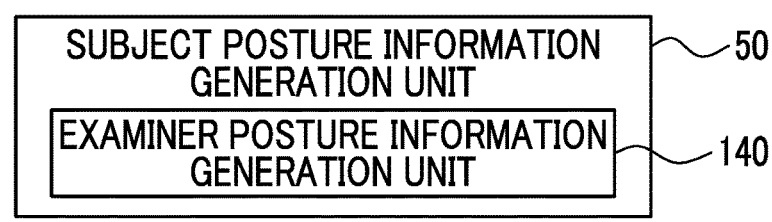
FIG. 20 is a block diagram showing a function of a subject posture information generation unit.

The console 12 may generate examiner posture information indicating the posture of the examiner in addition to the subject posture information. Further, the notification with respect to the examiner and/or control of stopping the movable portion 22 may be performed by using the examiner positional relationship estimation information generated based on the examiner posture information and the movable portion position information. In this case, as shown in FIG. 20, the examiner posture information generation unit 140 is further provided in the subject posture information generation unit 50. It is preferable that the examiner posture information generation unit 140 extracts the examiner by performing the analysis processing on the distance measurement information, and generates the subject posture information which is the detailed posture information of the entire examiner by connecting the joint points of the examiner.

The analysis processing of generating the examiner posture information from the distance measurement information includes processing of extracting the distance measurement information of the examiner from the distance measurement information of all the detection targets. For example, in a case in which the detection target includes a plurality of persons, the subject and the examiner are extracted separately. In this case, the plurality of persons and the radiography apparatus may be extracted from the distance measurement information of all the detection targets, and identification information of the subject or the examiner may be given to each of the plurality of persons by using the positional relationship, the temporal change (movement), and the like between the plurality of persons and the radiography apparatus.

Figure 21:
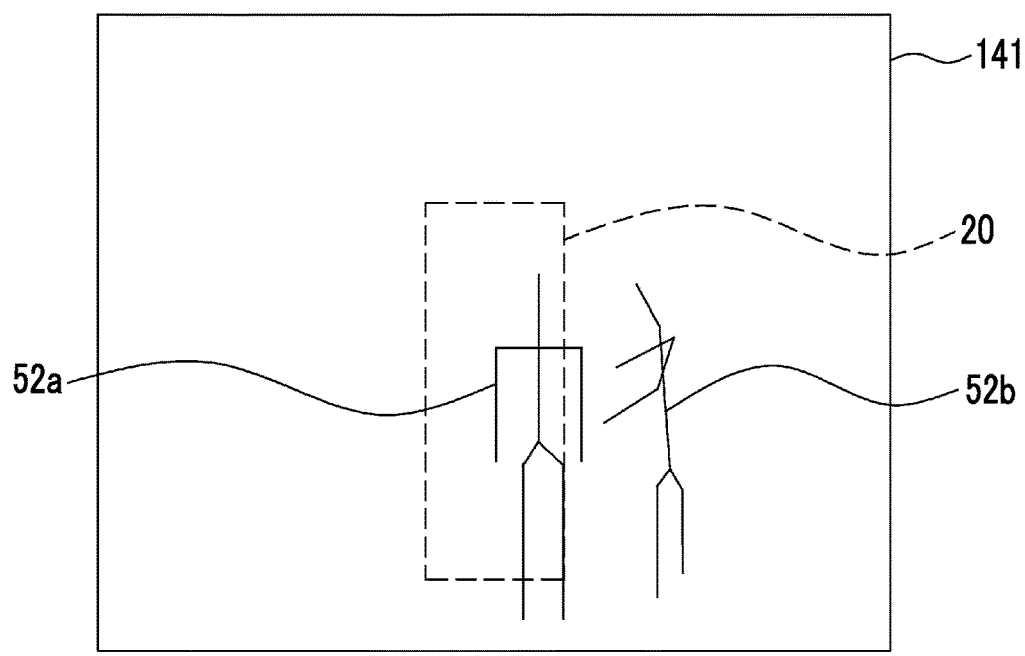
FIG. 21 is an explanatory diagram showing an example of a generation method of examiner posture information.

A specific example of the generation of the subject posture information will be described with reference to FIG. 21. FIG. 21 is a diagram showing an example of the information 141 used for the generation of the subject posture information. For example, the subject posture information generation unit 50 generates body axis information 52a and 52b indicating the body axes of the plurality of persons, and the apparatus posture information generation unit 60 generates the apparatus posture information indicating the mammography apparatus 20. In this case, the examiner posture information generation unit 140 may identify the body axis information 52a of the subject and the body axis information 52b of the examiner, which is the body axis information other than the body axis information 52a of the subject, and may generate the body axis information 52b of the examiner as the examiner posture information. The generated examiner posture information is transmitted to the positional relationship estimation information generation unit 70.

The positional relationship estimation information generation unit 70 receives the examiner posture information from the examiner posture information generation unit 140, and also receives the movable portion position information from the apparatus posture information generation unit 60. The positional relationship estimation information generation unit 70 generates the examiner positional relationship estimation information indicating the position, the posture, and/or the orientation of the examiner with respect to the movable portion 22 by using the position of the examiner indicated by the examiner posture information and the position of the movable portion 22 indicated by the movable portion position information. In this case, the imaging support information generation unit 71 determines the distance between the movable portion 22 and the examiner based on the examiner positional relationship estimation information. In a case in which it is determined that the distance between the movable portion 22 and the examiner is too close, the notification control information for giving notification to the examiner is generated, or the imaging apparatus control information for stopping the movable portion 22 is generated.

In the determination of the distance between the movable portion 22 and the examiner, for example, a specific distance between the movable portion and the examiner, which is any value, is set in advance for the distance between the movable portion 22 and the examiner, and it is determined that the distance between the movable portion 22 and the examiner is too close in a case in which the distance between the movable portion 22 and the examiner is smaller than the specific distance between the movable portion and the examiner. In addition, in a case in which the distance between the movable portion 22 and the examiner is equal to or greater than the specific distance between the movable portion and the examiner, it is determined that the distance between the movable portion 22 and the examiner is appropriate.

In this case, the notification controller 80 emits a warning sound, the voice message, or the like as the notification control of performing the notification to the examiner. In addition, the apparatus position controller 90 performs the imaging apparatus control of stopping the movement of the movable portion 22 in the vertical direction or the rotation thereof. With the configuration described above, it is possible to prevent the movable portion 22 from colliding with the examiner.

The console 12 may perform the imaging apparatus control of switching a mode of the radiography apparatus 13 based on the positional relationship estimation information. In this case, the radiography apparatus 13 can switch between an examination mode and a sleep mode. The examination mode is a mode in which the radiation source, the movable portion 22, and the like can be operated, and the radiation image can be captured. The sleep mode is a mode in which the operation related to the capturing of the radiation image or the function related to the operation is stopped, and the power-saving state is preferentially maintained.

The imaging support information generation unit 71 that receives the positional relationship estimation information determines the distance between the subject and the mammography apparatus 20 from the position of the subject with respect to the mammography apparatus 20. The imaging support information generation unit 71 generates the imaging apparatus control information instructing the subject to release the sleep mode and switch to the examination mode in a case in which it is determined that the distance between the subject and the mammography apparatus 20 is sufficiently close.

The determination of the distance between the subject and the mammography apparatus 20 is performed, for example, by setting, in advance, a specific distance for mode switching, which is any value, for the distance between the subject and the mammography apparatus 20. For example, in a case in which the distance between the subject and the mammography apparatus 20 is equal to or greater than the specific distance for mode switching, it is determined that the distance between the subject and the mammography apparatus 20 is sufficiently close. On the other hand, in a case in which the distance between the subject and the mammography apparatus 20 is less than the specific distance for mode switching, it is determined that the distance between the subject and the mammography apparatus 20 is not sufficiently close. With the configuration described above, it is possible to smoothly capture the radiation image in a case in which the examiner moves near the mammography apparatus 20. In addition, the power consumption can be saved in a case in which the subject is not positioned near the mammography apparatus 20.

Figure 22:
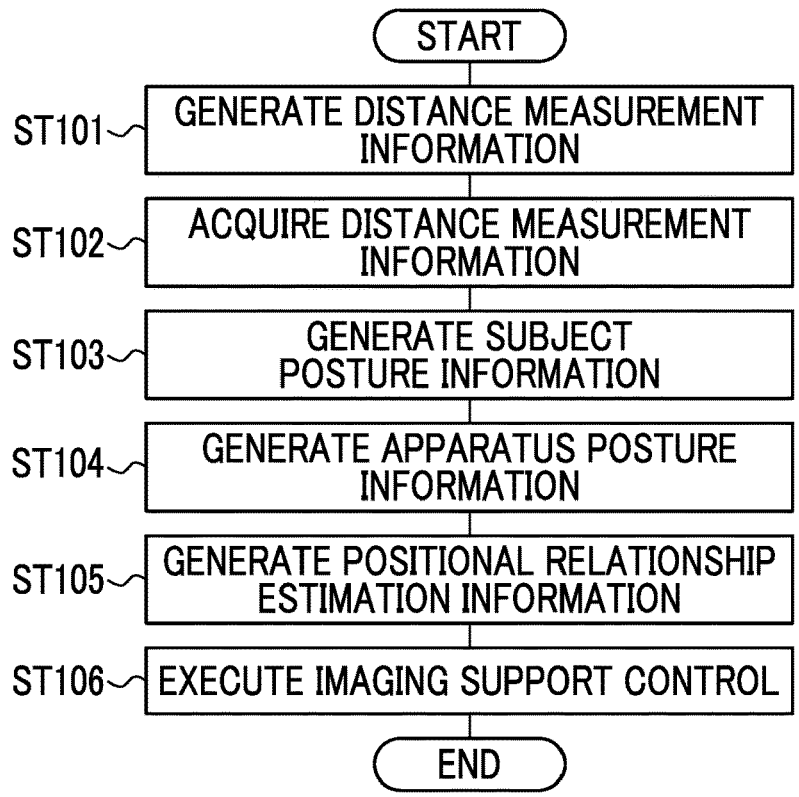
FIG. 22 is a flowchart showing a flow of performing imaging apparatus control or notification control by the radiography system.

The flow from the generation of the distance measurement information by the distance measurement device 11 to the imaging support control by the console 12 that acquires the distance measurement information will be described with reference to the flowchart shown in FIG. 22. First, the distance measurement device 11 emits the detection signal to receive the reflection signal from the detection target object and generates the distance measurement information based on the reflection signal (step ST101). Then, the distance measurement information acquisition unit 40 of the console 12 acquires the distance measurement information (step ST102). Then, the subject posture information generation unit 50 generates the subject posture information based on the distance measurement information (step ST103). Then, the apparatus posture information generation unit 60 generates the apparatus posture information based on the distance measurement information (step ST104). It should be noted that the step of generating the subject posture information and the step of generating the apparatus posture information may be in the reverse order. Then, the positional relationship estimation information generation unit 70 generates the positional relationship estimation information based on the subject posture information and the apparatus posture information (step ST105). Then, the imaging support information generation unit 71 generates the notification control information and transmits the generated notification control information to the notification controller 80, or generates apparatus position control information and transmits the generated apparatus position control information to the apparatus position controller 90. Finally, the notification controller 80 performs the notification control, or the apparatus position controller 90 executes the imaging support control of performing the imaging apparatus control (step ST106).

Second Embodiment

In the first embodiment, as shown in FIGS. 5 and 6, since the distance measurement device 11 is installed at the position spaced from the radiography apparatus 13 (mammography apparatus 20 in FIGS. 5 and 6), the radiography apparatus 13 is included in the detection target. In the second embodiment, the distance measurement device 11 is built in or externally attached to the radiography apparatus 13. In the second embodiment, the distance measurement device 11 is built in or externally attached to the radiography apparatus 13, so that the radiography apparatus 13 is not included in the detection target. In such a case in which the radiography apparatus 13 is not included in the detection target object, the apparatus posture information is acquired as a fixed value indicating the positional relationship between the distance measurement device 11 and the radiography apparatus 13, or a value calculated from a movement amount from the fixed value.

Figure 23:
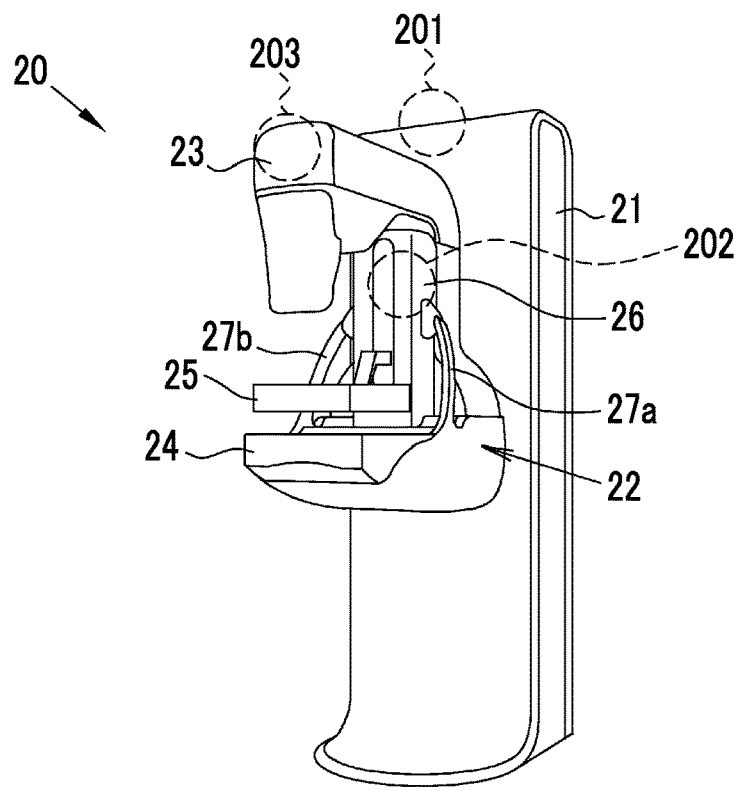
FIG. 23 is an explanatory diagram showing a position of a distance measurement device according to a second embodiment.

In the second embodiment, for example, the distance measurement device 11 is built in or externally attached to installation positions 201, 202, and 203 of the radiography apparatus 13 (mammography apparatus 20 in FIG. 23) as shown in FIG. 23. The installation position 201 is the stand portion 21, and is a position at which visibility is good and the position of the distance measurement device 11 can be fixed. The installation position 202 is the raising and lowering portion 26 included in the movable portion 22. The installation position 203 is a position in the vicinity of the radiation generation unit 23 provided in the movable portion 22. The installation position of the distance measurement device 11 is not limited to the position shown in FIG. 23, and need only be a position at which the distance measurement information on the detection target, such as the subject, the examiner, and the examination room, can be appropriately generated and acquired. The example in which the distance measurement device 11 is built in or externally attached to the movable portion 22 is suitable from the viewpoint of avoiding a collision between the movable portion 22 and the subject or the examiner.

In a case in which the distance measurement device 11 is built in or externally attached to a fixed installation position, such as the stand portion 21, the apparatus posture information is a fixed value input to the console 12 in advance. In this case, the apparatus posture information generation unit 60 acquires the apparatus posture information as the positional relationship between the distance measurement device 11 and the radiography apparatus 13 as a fixed value that is input to the console 12 in advance, and transmits the acquired apparatus posture information to the positional relationship estimation information generation unit 70. Further, the positional relationship between the distance measurement device 11 and the radiography apparatus 13 is transmitted to the positional relationship estimation information generation unit 70 even in a case in which there is no information about a clear position of the radiography apparatus 13. For example, since the distance measurement device 11 and the radiography apparatus 13 are positioned at substantially the same position, it is assumed that the apparatus posture information is substantially unnecessary. However, even in such a case, the positional relationship between the distance measurement device 11 and the radiography apparatus 13 indicating that the distance measurement device 11 and the radiography apparatus 13 are positioned at substantially the same position may be included as an example of the apparatus posture information.

In a case in which the distance measurement device 11 is built in or externally attached to the movable portion 22 that moves in the vertical direction or rotates, the apparatus posture information may be calculated from the movement amount from the fixed value input to the console 12 in advance. In a case in which the apparatus posture information is calculated as the value calculated from the movement amount from the fixed value, for example, the apparatus posture information is calculated by defining the position of the distance measurement device 11 in a stationary state in the sleep mode is set as a reference position and the position of the distance measurement device 11 after the movement in the vertical direction or after the movement due to the rotation as a post-movement position, and adding a difference between the reference position and the post-movement position as the movement amount to the fixed value. In this case, the apparatus posture information generation unit 60 is provided with an apparatus posture information calculation unit (not shown), and the apparatus posture information calculation unit calculates the apparatus posture information. The calculated apparatus posture information is transmitted to the positional relationship estimation information generation unit 70.

Similarly, the movable portion position information is also set as a fixed value input to the console 12 in advance or the value calculated from the movement amount from the fixed value, and is transmitted from the apparatus posture information generation unit 60 to the positional relationship estimation information generation unit 70.

Figure 24:
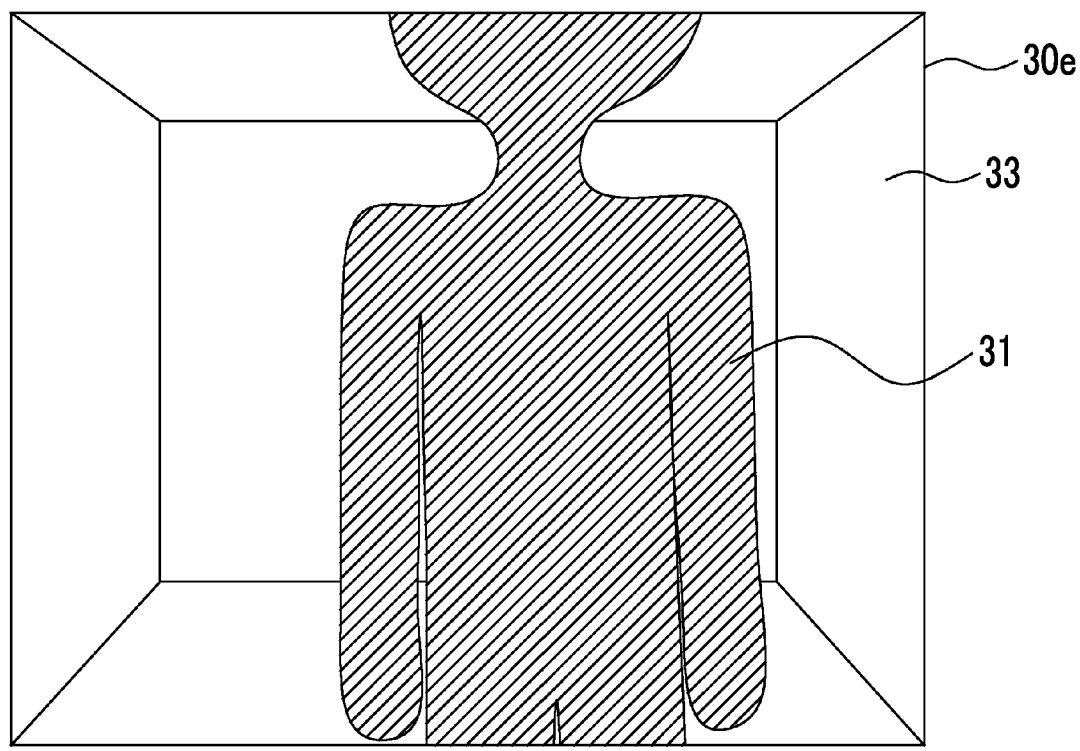
FIG. 24 is an explanatory diagram showing an example of distance measurement information generated in a case in which the distance measurement device is built in or externally attached to the mammography apparatus.

In a case in which the distance measurement device 11 is built in or externally attached to the installation position 202 in the second embodiment, the console 12 acquires distance measurement information 30e as shown in FIG. 24, for example. FIG. 24 shows the distance measurement information 30e in a case in which an abdominal side of the subject faces the mammography apparatus 20. The subject posture information generation unit 50 generates the subject posture information based on the distance measurement information 30e.

The positional relationship estimation information generation unit 70 generates the positional relationship estimation information by using the subject posture information and the apparatus posture information. The subsequent flow of performing the notification control or the apparatus position control based on the positional relationship estimation information is the same as that of the first embodiment, and thus the description thereof will be omitted. In addition, in the second embodiment, the functions of the distance measurement information generation unit 30 of the distance measurement device 11, and the distance measurement information acquisition unit 40, the subject posture information generation unit 50, the positional relationship estimation information generation unit 70, the notification controller 80, the apparatus position controller 90, the imaging position information generation unit 120, the imaging preparation comparison information generation unit 130, and the examiner posture information generation unit 140 of the console 12 are the same as those of the first embodiment, and thus the description will be omitted.

In the second embodiment in which the distance measurement device 11 is built in or externally attached to the radiography apparatus 13, since the positional relationship (or the reference position of the distance measurement device 11) between the distance measurement device 11 and the radiography apparatus 13 is a known fixed value, processing of generating the apparatus posture information based on the distance measurement information can be omitted, and as a result, the internal processing of the console 12 can be simplified. Also, the internal processing of the console 12 can be speeded up.

In the embodiments described above, the hardware structure of the processing unit that executes various types of processing, such as the distance measurement information acquisition unit 40, the subject posture information generation unit 50, the apparatus posture information generation unit 60, the positional relationship estimation information generation unit 70, the notification controller 80, the apparatus position controller 90, the imaging position information generation unit 120, the imaging preparation comparison information generation unit 130, and the examiner posture information generation unit 140, is the following various processors. Examples of the various processors include a central processing unit (CPU), which is a general-purpose processor that executes software (program) to function as various processing units, a programmable logic device (PLD), which is a processor of which a circuit configuration can be changed after manufacturing, such as a field programmable gate array (FPGA), and a dedicated electric circuit, which is a processor of which a circuit configuration is designed exclusively for executing various types of processing.

One processing unit may be configured by one of these various processors, or may be configured by a combination of two or more same type or different type of processors (for example, a plurality of FPGAs, or a combination of a CPU and an FPGA). In addition, a plurality of the processing units may be configured by one processor. As an example in which the plurality of processing units are configured by one processor, first, there is a form in which one processor is configured by a combination of one or more CPUs and software, and this processor functions as the plurality of processing units, as represented by a computer, such as a client or a server. Second, there is a form in which a processor, which realizes the functions of the entire system including the plurality of processing units with one IC chip, is used, as represented by a system on chip (SoC) or the like. As described above, various processing units are configured by one or more of the various processors described above, as the hardware structure.

Further, more specifically, the hardware structure of these various processors is an electric circuit (circuitry) having a form in which circuit elements, such as semiconductor elements, are combined. In addition, the hardware structure of the storage unit is a storage device, such as a hard disc drive (HDD) or a solid state drive (SSD).

EXPLANATION OF REFERENCES

10: radiography system
11: distance measurement device
12: console
13: radiography apparatus
20: mammography apparatus
21: stand portion
22: movable portion
23: radiation generation unit
24: imaging table
25: compression plate
26: raising and lowering portion
27a, 27b: grip portion
28: floor surface
30: distance measurement information generation unit
30a, 30b, 30c, 30d, 30e: distance measurement information
31: subject
32: detection signal
33: wall
34: auxiliary line
40: distance measurement information acquisition unit
50: subject posture information generation unit
51: subject posture information
52, 52a, 52b: body axis information
53: trunk axis
60: apparatus posture information generation unit
61: central axis
70: positional relationship estimation information generation unit
71: imaging support information generation unit
80: notification controller
81a, 81b, 81c, 81d: imaging support image
82: imaging support information display field
83: radiation image display field
84a, 84b, 84c, 84d, 84e: imaging instruction control button
85: warning display mark
86: imaging preparation information display field
87: text message
90: apparatus position controller
100: output unit
110: operation input unit
120: imaging position information generation unit
121: information for generating imaging position information
130: imaging preparation comparison information generation unit
140: examiner posture information generation unit 141: information for generating subject posture information
201, 202, 203: installation position
R: examination room

What is claimed is:

1. A radiography system comprising:
   a radiography apparatus that generates a radiation image by imaging a subject;
   a distance measurement device that generates distance measurement information about a detection target including the subject; and
   a processor configured to:
     acquire the distance measurement information;
     generate subject posture information indicating a posture of the subject based on the distance measurement information;
     generate positional relationship estimation information indicating a position, a posture, and/or an orientation of the subject with respect to the radiography apparatus by using the subject posture information and apparatus posture information indicating a posture of the radiography apparatus; and
     perform, based on the positional relationship estimation information, notification control of giving notification about capturing of the radiation image and/or imaging apparatus control for the radiography apparatus.

2. The radiography system according to claim 1,
   wherein the distance measurement device generates distance measurement information about the radiography apparatus, and
   the processor is configured to generate the apparatus posture information based on the distance measurement information.

3. The radiography system according to claim 2,
   wherein the subject posture information includes body axis information indicating a position of a body axis in a cranio-caudal direction of the subject, and
   the processor is configured to:
     determine whether the body axis in the cranio-caudal direction of the subject is a right breast imaging position that is a position for imaging a right breast of the subject or a left breast imaging position that is a position for imaging a left breast of the subject, by using the body axis information and the apparatus posture information; and
     generate imaging position information, which is the determination result, as the positional relationship estimation information.

4. The radiography system according to claim 3,
   wherein the processor is configured to perform, as the notification control, notification that the radiography apparatus captures the radiation image of the left breast of the subject or the right breast of the subject, based on the imaging position information.

5. The radiography system according to claim 3,
   wherein the processor is configured to:
     generate imaging preparation comparison information, which is a result of a comparison between the imaging position information and imaging preparation information, the imaging preparation information being input in advance for giving an instruction to image the left breast or the right breast of the subject; and
     perform the notification control or the imaging apparatus control based on the imaging preparation comparison information.

6. The radiography system according to claim 2,
   wherein the radiography apparatus includes an imaging table on which a breast of the subject is disposed, and a movable portion that moves in a vertical direction or rotates while maintaining a position relative to a radiation source that generates radiation, and
   the apparatus posture information includes movable portion position information indicating a position of the movable portion.

7. The radiography system according to claim 6,
   wherein the subject posture information includes breast position information indicating a position of a left breast and/or a right breast of the subject, and
   the processor is configured to:
     generate the positional relationship estimation information indicating a position of the left breast or the right breast of the subject with respect to the movable portion based on the breast position information and the movable portion position information; and
     perform, as the notification control, notification that a distance between the position of the breast and the position of the movable portion is equal to or greater than a specific imaging distance, based on the positional relationship estimation information.

8. The radiography system according to claim 6,
   wherein the subject posture information includes breast position information indicating a position of a left breast and/or a right breast of the subject, and
   the processor is configured to:
     generate the positional relationship estimation information indicating a position of the left breast or the right breast of the subject with respect to the movable portion based on the breast position information and the movable portion position information; and
     perform, as the imaging apparatus control, moving or rotating of the movable portion, based on the positional relationship estimation information.

9. The radiography system according to claim 6,
   wherein the distance measurement device generates the distance measurement information about an examiner different from the subject, and
   the processor is configured to:
     generate examiner posture information indicating a posture of the examiner based on the distance measurement information;
     generate examiner positional relationship estimation information indicating a position, a posture, and/or an orientation of the examiner with respect to the movable portion based on the examiner posture information and the movable portion position information; and
     perform notification to the examiner as the notification control and/or stop the movable portion as the imaging apparatus control, based on the examiner positional relationship estimation information.

10. The radiography system according to claim 2,
    wherein the distance measurement device emits a detection signal toward a back surface or a side surface of the subject.

11. The radiography system according to claim 1,
    wherein the processor is configured to acquire the apparatus posture information by using a positional relationship, which is input in advance, between the distance measurement device and the radiography apparatus.

12. The radiography system according to claim 1,
wherein the processor is configured to perform, as the imaging apparatus control, releasing of a sleep mode of the radiography apparatus based on the positional relationship estimation information.

13. The radiography system according to claim 1,
wherein the processor is configured to inputs the distance measurement information to a trained model and outputs the subject posture information.

14. An operation method of a radiography system, the method comprising:
- a step of generating distance measurement information about a detection target including a subject;
- a step of acquiring the distance measurement information;
- a step of generating subject posture information indicating a posture of the subject based on the distance measurement information;
- a step of generating positional relationship estimation information indicating a position, a posture, and/or an orientation of the subject with respect to a radiography apparatus that generates a radiation image by imaging the subject, by using the subject posture information and apparatus posture information indicating a posture of the radiography apparatus; and
- a step of performing, based on the positional relationship estimation information, notification control of giving notification about capturing of the radiation image and/or imaging apparatus control for the radiography apparatus.

15. A radiography control apparatus that performs:
notification control of giving notification about capturing of a radiation image and/or imaging apparatus control for a radiography apparatus, based on positional relationship estimation information indicating a position, a posture, and/or an orientation of a subject with respect to the radiography apparatus, the positional relationship estimation information being obtained from subject posture information obtained from distance measurement information from a distance measurement device and apparatus posture information indicating a positional relationship of the radiography apparatus.

* * * * *